US008983619B2

(12) United States Patent
Cinbis et al.

(10) Patent No.: US 8,983,619 B2
(45) Date of Patent: Mar. 17, 2015

(54) TESTING COMMUNICATION DURING IMPLANTATION

(75) Inventors: Can Cinbis, Shoreview, MN (US); H. Toby Markowitz, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1255 days.

(21) Appl. No.: 12/732,403

(22) Filed: Mar. 26, 2010

(65) Prior Publication Data
US 2011/0160557 A1 Jun. 30, 2011

Related U.S. Application Data

(60) Provisional application No. 61/291,098, filed on Dec. 30, 2009.

(51) Int. Cl.
*A61N 1/08* (2006.01)
*A61B 5/00* (2006.01)
*A61N 1/372* (2006.01)
(Continued)

(52) U.S. Cl.
CPC ............. *A61B 5/0028* (2013.01); *A61B 5/0031* (2013.01); *A61N 1/37217* (2013.01); *A61B 2019/5253* (2013.01); *A61B 2560/0271* (2013.01); *A61N 1/37205* (2013.01); *A61N 1/37241* (2013.01); *A61N 1/3756* (2013.01)
USPC .................................. 607/60; 607/30; 607/61

(58) Field of Classification Search
CPC ............... A61B 5/0028; A61B 5/0031; A61N 1/37217; A61N 1/37205; A61N 1/37211
USPC .......................................... 607/30, 32, 60, 61
See application file for complete search history.

(56) References Cited

U.S. PATENT DOCUMENTS

| 4,603,705 A | 8/1986 | Speicher et al. |
| 4,987,897 A | 1/1991 | Funke |

(Continued)

FOREIGN PATENT DOCUMENTS

| WO | 0059376 | 10/2000 |
| WO | 2006012630 | 2/2006 |
| WO | 2009/056167 | 5/2009 |

OTHER PUBLICATIONS (PCT/US2010/060762) PCT Notification of Transmittal of the International Search Report and the Written Opinion of the International Searching Authority, Mailed May 10, 2011, 12 pages.
(Continued)

*Primary Examiner* — Tammie K Heller
(74) *Attorney, Agent, or Firm* — Michael J. Ostrom; Stephen W. Bauer

(57) ABSTRACT

A system and method are described for testing communication through a patient during implantation using telemetry coupling electrodes on a delivery catheter. In one example, at least two telemetry coupling electrodes may be placed on or within a delivery catheter to test conductive communication with external body electrodes during implantation. In some instances, the telemetry coupling electrodes of the delivery catheter may approximate the spacing of telemetry electrodes on an IMD. In this manner, testing conductively coupled communication with telemetry coupling electrodes of the catheter may be used to mimic the telemetry electrodes on the IMD and determine a target position and/or orientation of an electrode or electrodes of the IMD for successful conductive communication through the body.

8 Claims, 22 Drawing Sheets

(51) Int. Cl.
 *A61B 19/00* (2006.01)
 *A61N 1/375* (2006.01)

(56) References Cited

U.S. PATENT DOCUMENTS

| | | | |
|---|---|---|---|
| 5,697,377 | A | 12/1997 | Wittkampf |
| 5,983,126 | A | 11/1999 | Wittkampf |
| 6,009,878 | A | 1/2000 | Weijand et al. |
| 6,112,116 | A | 8/2000 | Fischell et al. |
| 2006/0020300 | A1 | 1/2006 | Nghiem et al. |
| 2006/0241732 | A1 | 10/2006 | Denker et al. |
| 2007/0123947 | A1 | 5/2007 | Wenger et al. |
| 2007/0203546 | A1 | 8/2007 | Stone et al. |
| 2008/0269763 | A1 | 10/2008 | Bonde et al. |
| 2009/0018599 | A1 | 1/2009 | Hastings et al. |
| 2009/0030288 | A1 | 1/2009 | Abboud et al. |
| 2009/0253985 | A1 | 10/2009 | Shachar et al. |
| 2009/0276020 | A1 | 11/2009 | Nee et al. |
| 2009/0318995 | A1 | 12/2009 | Keel et al. |
| 2010/0016840 | A1 | 1/2010 | Stahmann et al. |
| 2011/0160801 | A1 | 6/2011 | Markowitz et al. |

OTHER PUBLICATIONS (PCT/US2010/060752) PCT Notification of Transmittal of the International Search Report and the Written Opinion of the International Searching Authority, Mailed May 12, 2011, 11 pages.

Response to Final Office Action dated Apr. 5, 2013, from U.S. Appl. No. 12/732,433, filed Jun. 5, 2013, 7 pp.

Advisory Action dated Jun. 13, 2013, from U.S. Appl. No. 12/732,433, 3 pp.

Response to Final Office Action dated Apr. 5, 2013 and Advisory Action mailed Jun. 13, 2013, from U.S. Appl. No. 12/732,433, filed Jul. 3, 2013, 15 pp.

Office Action from co-pending U.S. Appl. No. 12/732,433 dated Apr. 5, 2013 (11 pages).

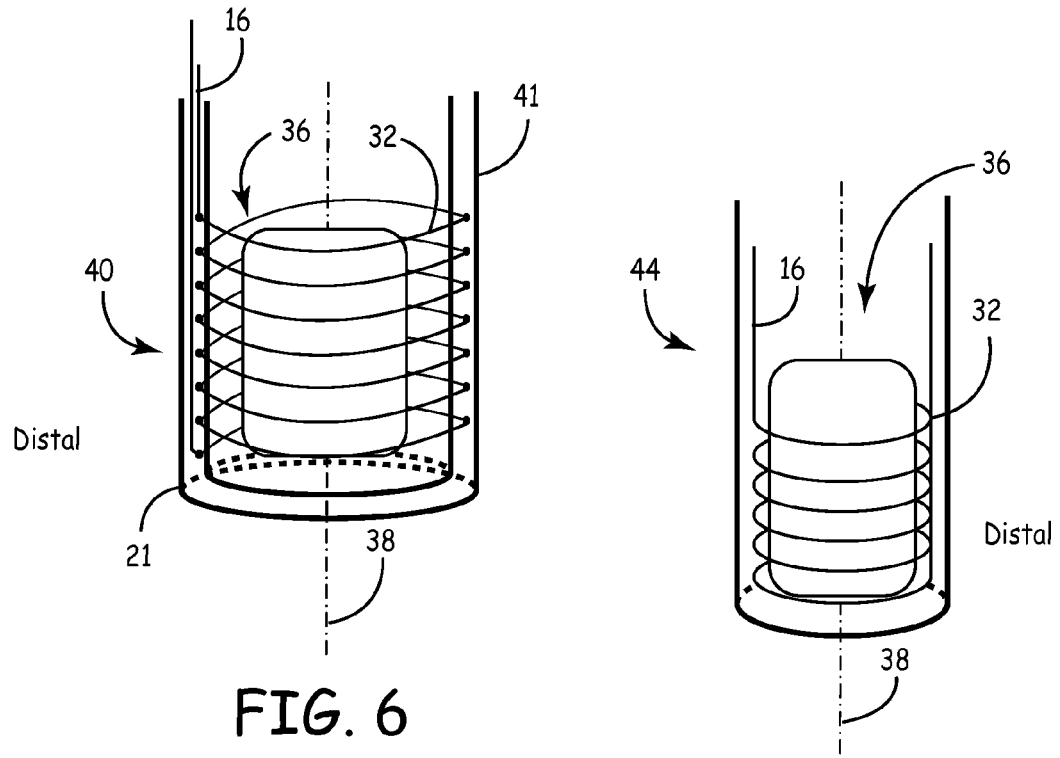
FIG. 6
FIG. 7
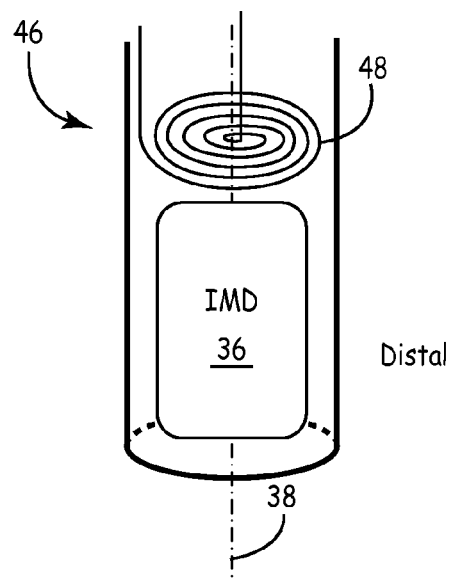
FIG. 8

TESTING COMMUNICATION DURING IMPLANTATION

This application claims the benefit of U.S. Provisional Application No. 61/291,098, filed on Dec. 30, 2009. The entire disclosure of the above application is incorporated herein by reference.

TECHNICAL FIELD

The disclosure relates generally to devices and methods for testing communication through a patient during implantation using telemetry coupling electrodes.

BACKGROUND

A wide variety of implantable medical devices (IMDs) that deliver a therapy to or monitor a physiologic or biological condition of a patient, or both, have been clinically implanted or proposed for clinical implantation in patients. An IMD may deliver therapy to or monitor a physiological or biological condition with respect to a variety of organs, nerves, muscles or tissues of the patients, such as the heart, brain, stomach, spinal cord, pelvic floor, or the like. The therapy provided by the IMD may include electrical stimulation therapy, drug delivery therapy or the like.

The IMD may exchange telemetry communications with one or more other devices. The IMD may exchange telemetry communications with an external device, such as a programmer device or a patient monitor (e.g., either attached to the patient or otherwise located near the patient). This information may be previously stored or real-time information. The IMD may also receive information from another device, such as the programmer, via telemetry communication. Telemetry communication, however, requires a considerable current drain as compared to the current drawn during non-telemetry operations during the service life of the IMD. As such, extensive telemetry communication with the IMD drains the power source of the IMD of valuable energy that could otherwise extend the service life of the IMD.

Some IMDs may include one or more leads that extend from the IMD to a target location of a patient, e.g., target organ, nerve, muscle or tissue of the patient. In one example, the IMD may include one or more leads that extend to target locations within a heart of the patient. Other IMDs, however, may be sufficiently small that the IMD may be placed directly at the target location without the need for one or more leads extending from the IMD. Such a device may be referred to as a leadless IMD.

During implantation of an IMD that utilizes a conventional lead(s), the proximal end of the lead(s) is first connected to an analyzer to verify good connection to a target location which is suitable for stimulation and/or detection as well as intact conduction and insulation along the lead. The analyzer may be a stand alone external instrument or integrated within other instrumentation such as a programmer or cardiac navigation system. During implantation of an IMD without conventional leads (e.g., using a delivery catheter), wireless telemetry communication between the IMD and an external device is used to verify good connection to the target location suitable for stimulation and detection. This is because the IMD may not have a connection readily available for use with an analyzer.

SUMMARY

This disclosure describes techniques for testing communication through a patient during implantation using telemetry coupling electrodes. In one example, at least two telemetry coupling electrodes may be placed on or within a delivery catheter to test conductive communication with external body electrodes during implantation. In some instances, the telemetry coupling electrodes of the delivery catheter may approximate the spacing of telemetry electrodes on an IMD. In this manner, testing conductively coupled communication with telemetry coupling electrodes of the catheter may be used to mimic the telemetry electrodes on the IMD. In this manner, a user may determine a target position and/or orientation of an electrode or electrodes of the IMD for successful conductive communication through the body. Using telemetry coupling electrodes on the catheter may reduce the amount of power consumed during implantation of the IMD by no longer requiring the IMD to transmit the communications to determine suitable conductive communication.

In one example, this disclosure is directed to an implantable medical device delivery system comprising a catheter located at least partially within a patient, the catheter comprising an elongate catheter body having a proximal end and a distal end at least two telemetry coupling electrodes located on the distal end of the catheter body; and a feed line coupled to the telemetry coupling electrode. The system further includes at least one body electrode on the patient and an external device coupled to the feed line at the proximal end of the catheter and to the body electrode. The external device generates and receives a communication signal that is communicated through the patient between the body electrode and the telemetry coupling electrodes.

In another example, this disclosure is directed to a method for testing communication through a patient between at least two telemetry coupling electrodes and a body electrode on a patient. The method comprises communicating a signal between at least one body electrode on a patient and at least two telemetry coupling electrodes on a distal end of a catheter within the patient and measuring a signal quality of the communication through the patient between the telemetry coupling electrodes and the body electrode.

In a further example, this disclosure is directed to a system for testing communication through a patient comprising means for conductively coupling to the patient noninvasively, means for conductively coupling to the patient invasively, means for generating and receiving a communication signal, means for coupling the signal means with the invasive means and the noninvasive means, means for communicating through the patient between the noninvasive means and the invasive means via the signal means, means for measuring a quality of the communication through the patient between the noninvasive means and the invasive means.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF THE DRAWINGS

FIG. 6 is a conceptual diagram illustrating detail of the distal end of an example catheter with an antenna and feed line embedded in the body of the catheter.

FIG. 7 is a conceptual diagram illustrating detail of the distal end of an example catheter with a feed line and an antenna surrounding an IMD.

FIG. 8 is a conceptual diagram illustrating detail of an example distal end of a catheter with a feed line and a planar antenna.

FIG. 10b is a conceptual diagram illustrating detail of the example IMD in FIG. 10a.

FIG. 11b is a conceptual diagram illustrating detail of the example IMD in FIG. 11a.

DETAILED DESCRIPTION

Some IMDs for delivering a therapy and/or monitoring a condition of a patient are sufficiently small such that the IMD may be placed directly at the target location without the need for one or more leads extending from the IMD and connecting the IMD to the target location. Such IMDs, which may be referred to as leadless IMDs, are typically implanted within a patient using a delivery catheter. The delivery catheter may be designed to deliver the IMD into the body of the patient. The catheter is indwelling, that is, it is placed at least partially into the body of the patient to deliver the IMD from outside the patient to inside the patient. Various techniques are well known for gaining access to the interior of the patient utilizing the cardiovascular vessels and other spaces within the body. In the example of cardiac rhythm management devices, the Seldinger technique may be used to access the patient's venous anatomy. Puncturing the skin below the xiphoid process may also be used to gain access to the pericardial space. The techniques just mentioned generally do not require general anesthesia nor do they require depressing respiratory function. However, any of a variety of other techniques may be used to gain access to the interior of the patient. Placement of small medical devices via a catheter may avoid the undesired cosmetic effects associated with the placement of similar devices placed through an incision in the skin, especially for the slender patient.

The catheter used for introduction and placement of an IMD may have the capability of being controlled external to the patient such that the catheter may be steered or pointed. The catheter is used to move the IMD to a suitable site for implantation. The suitable site for implantation may be referred to in this disclosure as a target location within the patient, and may include, a target organ, tissue, nerve, muscle or other location. Instrumentation may be provided for assessment of potential implant sites. Upon locating a suitable site for implantation, the IMD may be attached or located in the body in a manner such that it may remain affixed in the desired location.

Figure 1:
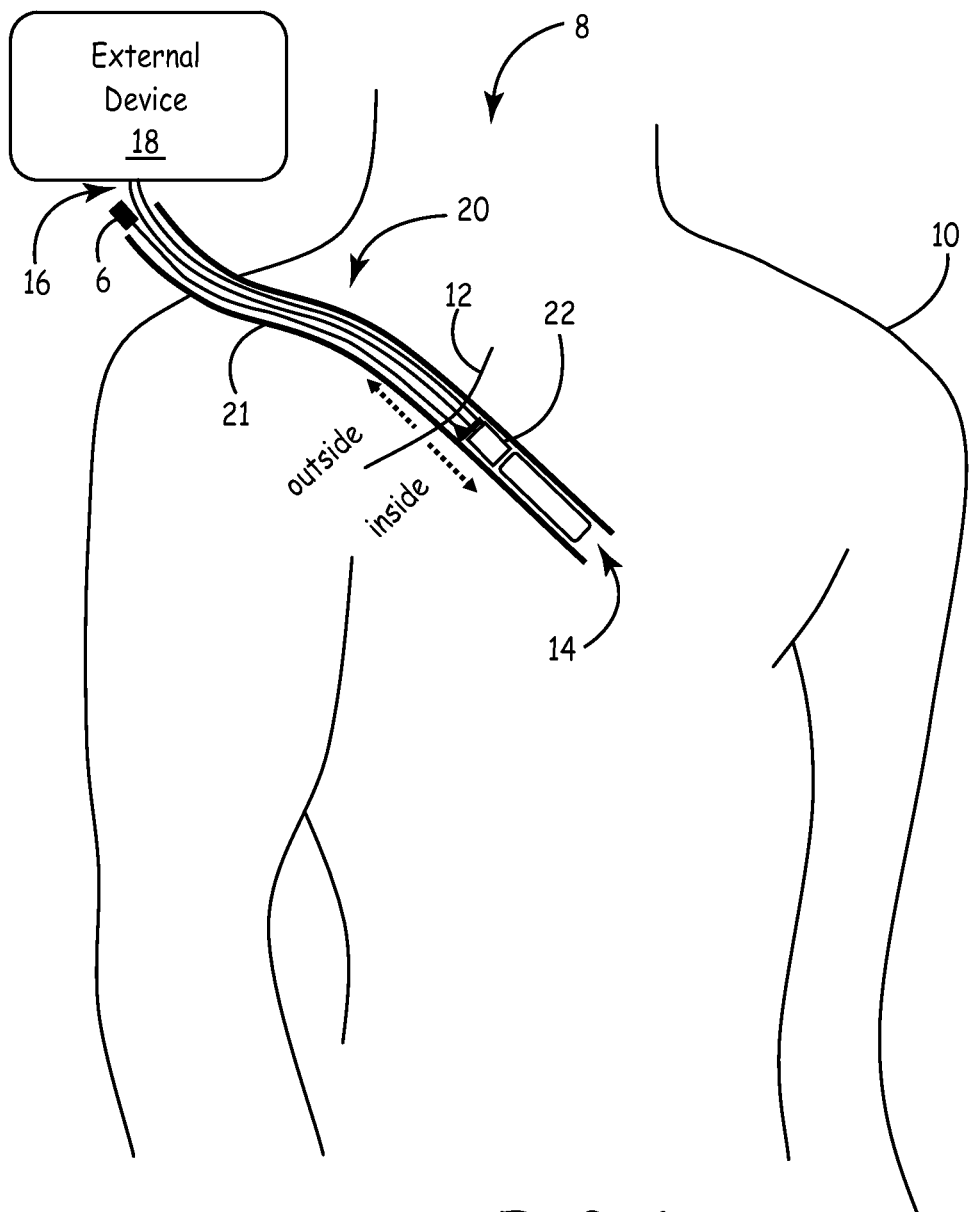
FIG. 1 is a conceptual diagram illustrating an example medical system in which a telemetry device is connected via a feed line to a telemetry coupling member placed in proximity to an IMD within a catheter.

FIG. 1 is a schematic diagram illustrating an example implantable medical device delivery system 8 for implanting an IMD 14 at a target location within a patient 10. Delivery system 8 includes a delivery catheter 20 that is placed partially within patient 10 via access site 12. The demarcation of access site 12 identifies the location at which the delivery catheter 20 transitions from outside patient 10 to inside patient 10. Although access site 12 is shown in FIG. 1 to be located in a chest area of patient 10, access site 12 may be located anywhere on the body of patient 10.

Delivery catheter 20 comprises an elongate catheter body 21 having a proximal end and a distal end. In the example illustrated in FIG. 1, the distal end of catheter body 21 is located within the body of patient 10 and the proximal end of catheter body 21 is located outside of the body of patient 10. Catheter body 21 may be constructed of soft, flexible materials such as silicone rubber or various elastomers. Delivery catheter 20 further comprises a telemetry coupling member 22 located near the distal end of catheter body 21 and a feed line 16 that extends from telemetry coupling member 22 to the proximal end of catheter body 21. Feed line 16 carries telemetry signals to and from telemetry coupling member 22.

Delivery catheter 20 may also include IMD 14 detachably coupled to the distal end of catheter body 21. IMD 14 may be placed in the delivery catheter 20 before delivery catheter 20 is placed at least partially within patient 10. For example, delivery catheter 20 may be shipped to a physician with IMD 14 placed within delivery catheter 20. As another example, delivery catheter 20 may be shipped to a physician without IMD 14 placed within delivery catheter 20 and the physician may place IMD 14 into delivery catheter 20 before delivery catheter 20 is received in patient 10. Alternatively, IMD 14 may be delivered from outside patient 10 to inside patient 10 through delivery catheter 20 after delivery catheter 20 is placed at least partially within patient 10.

IMD 14 may include appropriate circuitry and/or components for therapeutic and monitoring objectives during the service life of IMD 14. As will be described in further detail below, IMD 14 may, in one example, comprise one or more sensing components, therapy delivery components, telemetry components, power sources, memory components and the like. IMD 14 will be described in this disclosure as an implantable cardiac pacemaker for purpose of illustration. However, IMD 14 could be any of a number of medical devices intended for implantation in patients, such as a cardiac defibrillator, cardioverter and/or cardiac resynchronization device, a neurological stimulator, monitoring devices for a variety of physiological parameters, a pump for administering a drug or a biologic, or a replacement valve. The use of a cardiac pacemaker is illustrative of the concept but does not limit the applicability of the techniques as described herein.

Delivery catheter 20 may include a steering mechanism (not shown) that allows operator to steer catheter 20. The steering mechanism may include one or more pull wires. These comprise a wire or multiple wires placed in the wall of catheter body 21 and may be connected to various levers at the proximal end, outside of the body. Delivery catheter 20 may further include additional wires placed through a lumen formed by catheter body 21 or within the walls of catheter body 21 to perform other functions. For example, an additional wire from the proximal end to the distal end may allow an operator to push IMD 14 from the distal end of catheter 20 and eject it from delivery catheter 20. With a combination of wires and levers, the additional wires may allow the operator to rotate IMD 14 to affix IMD 14 to the target location. Such a mechanism is illustrated in FIG. 1 with reference numeral 6. The pull wires in delivery catheter 20 may also be utilized for electrical conduction. In this embodiment, the pull wires might also be used as feed line 16 for telemetry communication and/or as control lines for connection to the analyzer module in the external device 18 (shown in FIG. 17 and discussed below) or to send power to/from the IMD or for connection to sensors placed within the delivery catheter 20 (shown in FIGS. 10a, 10b and discussed below).

Figure 2:
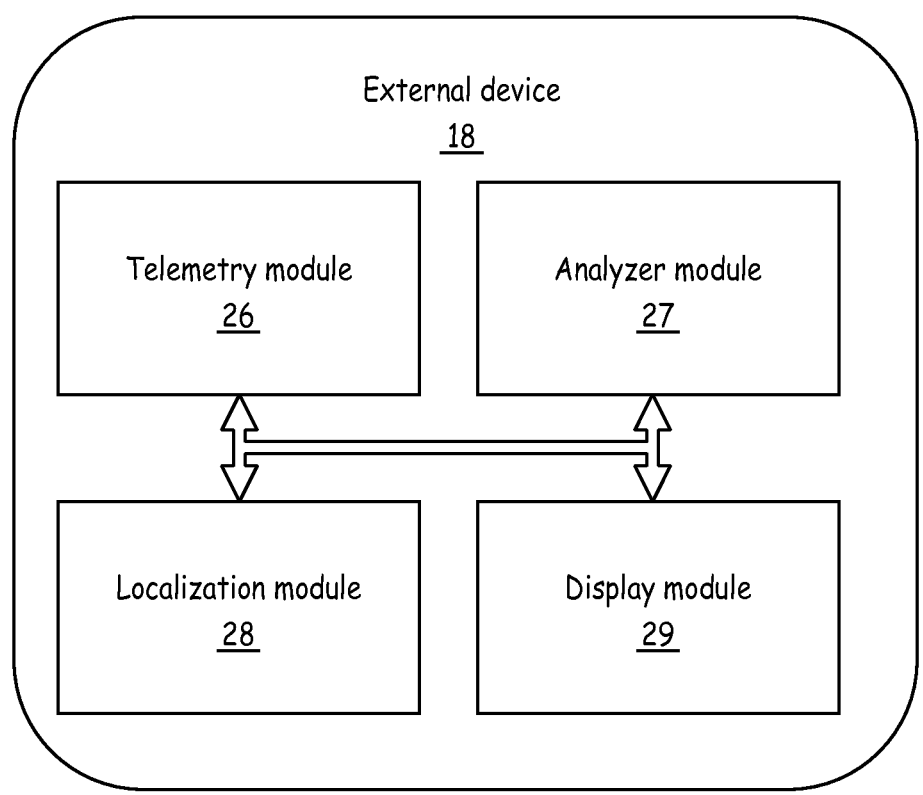
FIG. 2 illustrates an example external device comprising a telemetry module, an analyzer module, a localization module and a display module.

An external device 18 shown in FIG. 1 may also be part of delivery system 8. As illustrated in FIG. 2, the external device 18 comprises one or more of a telemetry module 26, an analyzer module 27, a localization module 28 and a display module 29. Telemetry module 26 may generate, receive and/or test telemetry communication signals for communicating with IMD 14. Analyzer module 27 may generate signals, receive signals, and direct testing measurements to assess the suitability of an electrode for implant considering the intended therapeutic use, monitoring use and telemetry communication. Localization module 28 may identify the position of IMD 14 or the electrodes of IMD 14 or other electrodes that are in or on the body of the patient 10. Display module 29 may present information for the clinician operator during a procedure using the external device, including information regarding the telemetry communication, testing, position, or other information. These modules and their functions are described below in further detail. While external device 18 of FIG. 2 is depicted comprising all four modules in one device, external device 18 may include only a portion of the modules and/or more include additional modules. Moreover, external device 18 may further comprise one or more separate devices, e.g., a telemetry device, an analyzer device, a localization device and/or a display device. In this manner, the modules of external device 18 may be constructed and combined in other combinations or all four could be separate.

Referring back to FIG. 1, during the navigation and delivery of IMD 14, it may be desirable for external device 18 to communicate with IMD 14. External device 18 may, for example, communicate with IMD 14 to cause IMD 14 to perform one or more actions including retrieving information verifying that the location of IMD 14 is suitable for one or more of stimulation, detection and telemetry communication. External device 18 of FIG. 1 is connected to feed line 16 at the proximal end of delivery catheter 20 to deliver electrical signals to and receive signals from the telemetry coupling member 22. The electrical signals delivered to telemetry coupling member 22 may be communicatively coupled to IMD 14, e.g., via any of a number of coupling techniques including, but not limited to, inductive coupling, conductive coupling, magnetic coupling, electromagnetic coupling, capacitive coupling, radio frequency (RF) coupling, electroacoustic coupling, electro-optical acoustic coupling, optical coupling, mechanical coupling, electrical coupling or the like.

Figure 3:
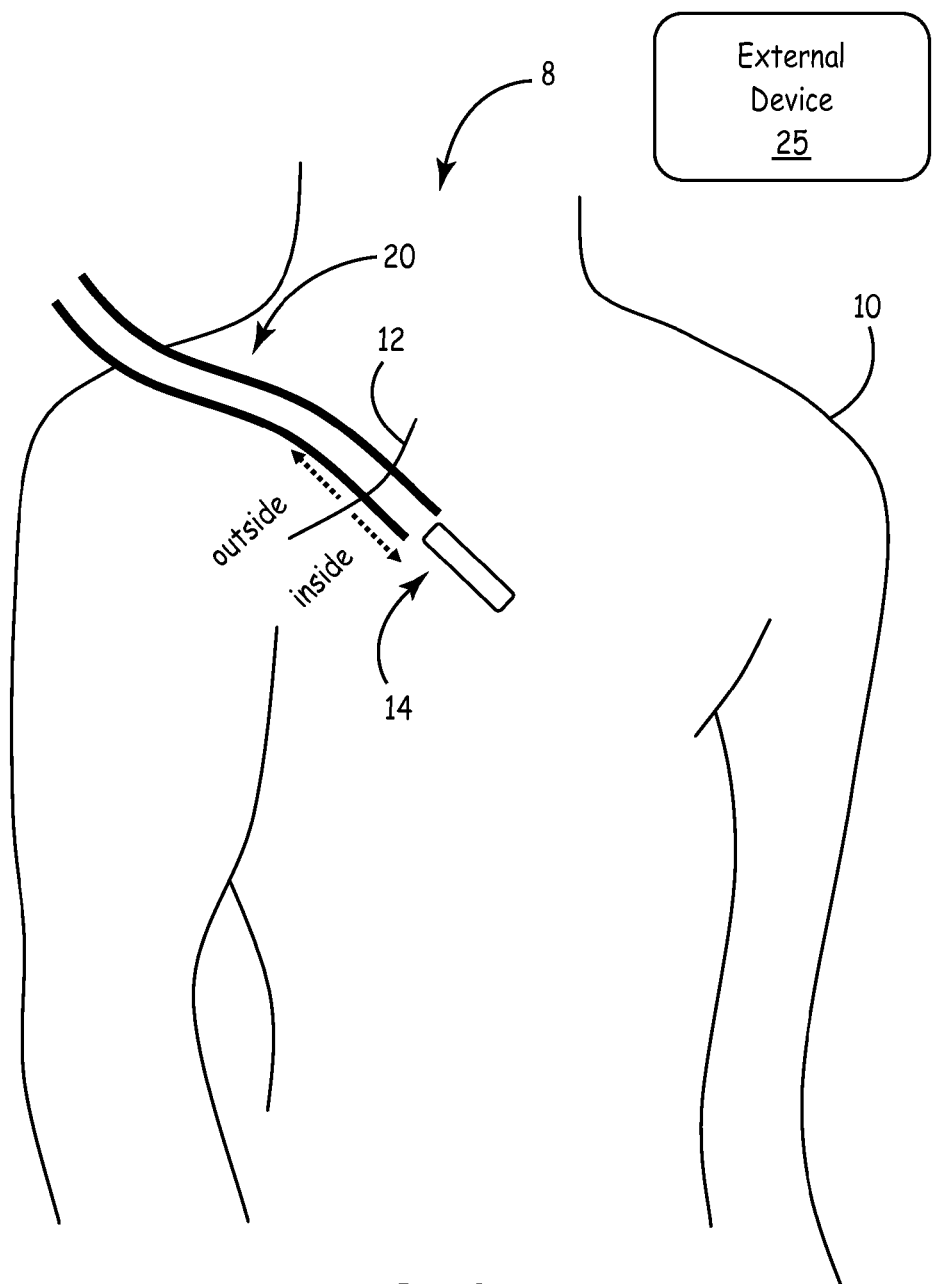
FIG. 3 is a schematic diagram illustrating an example IMD which has been expelled from a catheter. The IMD is communicating with an external device.

FIG. 3 is a schematic diagram illustrating implantable medical device delivery system 8 after IMD 14 is delivered to the target location within a patient 10. In other words, IMD 14 has been released from delivery catheter 20. After delivery of IMD 14 to the target location and expulsion from delivery catheter 20, IMD 14 may communicate with external device 25. External device 25 could be embodied as a programmer device or patient monitor device. External device 25 may, in some instances, correspond with external device 18. In other words, the same external device may be utilized to communicate with IMD 14 during implantation and after implantation. In other instances, external device 25 may be a different device.

External device 25 may allow a user, e.g., physician, clinician, nurse, technician or patient, to configure a therapy delivered by IMD 14 or to retrieve data sensed by IMD 14. External device 25 may include a user interface that receives input from the user and/or displays data to the user. External device 25 may be a dedicated hardware device with dedicated software for communicating with IMD 14. Alternatively, external device 25 may be an off-the-shelf computing device running an application that enables external device 25 to communicate with IMD 14. In some examples, external device 25 may be a handheld computing device that may be attached to or otherwise carried by patient 10. Alternatively, external device 25 may be a computer workstation, such as a CareLink® monitor, available from Medtronic, Inc. of Minneapolis, Minn.

Figure 4:
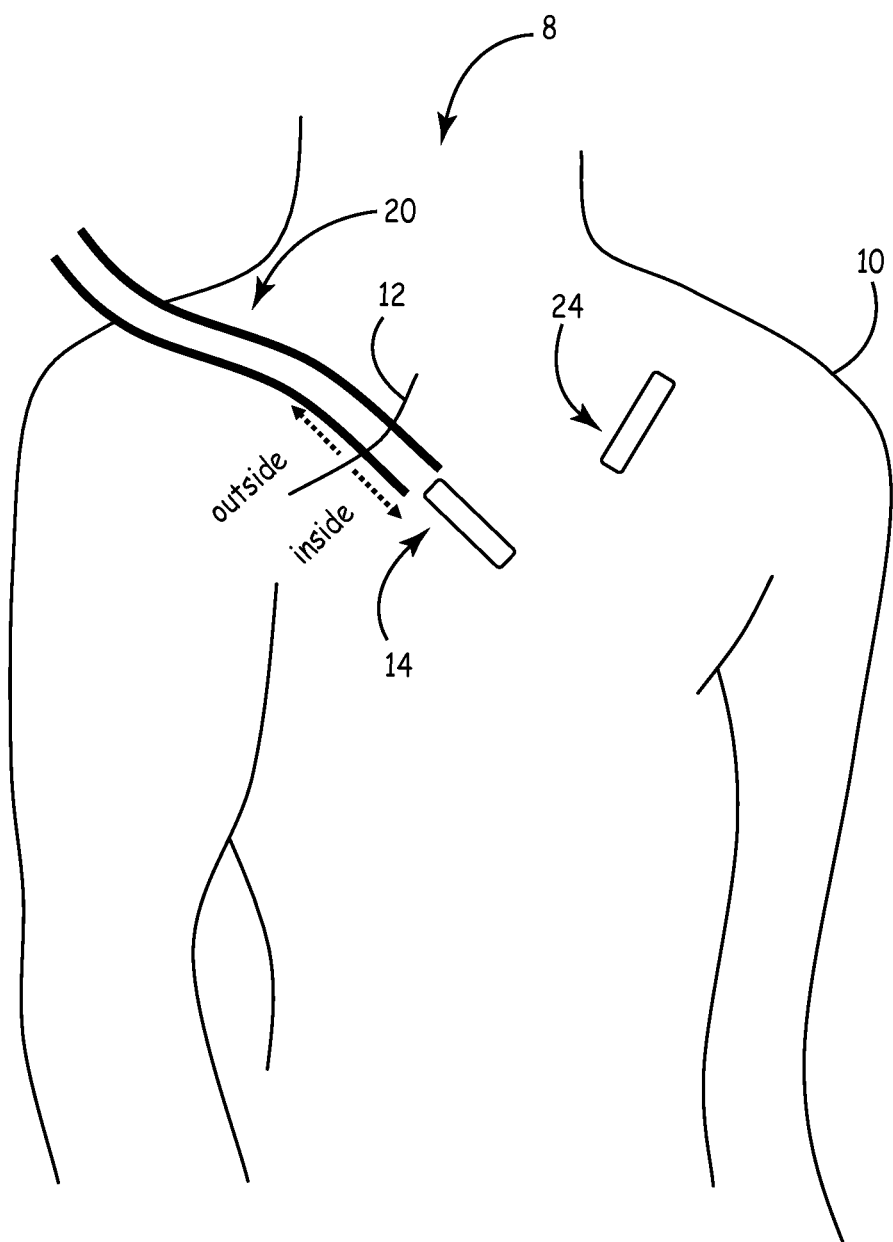
FIG. 4 is a schematic diagram illustrating an example IMD which has been expelled from a catheter. The IMD is communicating with another IMD.

IMD 14 may communicate with external device 18 and external device 25 by any of a number of wired and wireless communication techniques. As will be described in further detail herein, the communication techniques between IMD 14 and external device 18 during implantation may be different than the communication technique used to communicate between IMD 14 and external device 25 after implantation. In other instances, the communication technique between IMD 14 and external device 18 during implantation may be the same as the communication technique used once IMD 14 has been implanted, but with different amounts of power consumption. IMD 14 may also communicate with a second IMD 24 or other IMDs in addition to or instead of with external device 25, as shown in FIG. 4. Communication between IMD 14 and IMD 24 may use the same communication techniques as used between IMD 14 and external device 18 or different communication techniques.

Due to the small size of leadless IMDs, conservation of the energy within the power source of IMD 14 is desirable. Providing telemetry coupling member 22 (FIG. 1) within delivery catheter 20 allows power source energy to be conserved by a variety of methods, including delaying use of the IMD telemetry until IMD 14 has been implanted or using it in a low power mode until implantation is complete. Additionally, delivery catheter 20 eliminates the need to place a telemetry device in a sterile field and ensures the telemetry is reliably coupled to an external device, e.g., external device 25.

Figure 5:
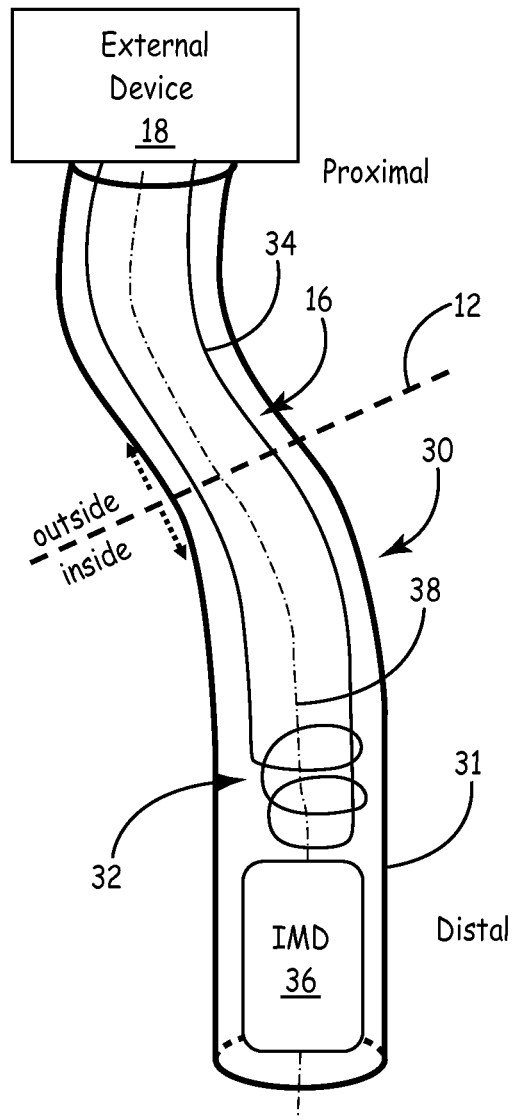
FIG. 5 is a schematic diagram illustrating a telemetry coupling member on the distal end of a catheter, the telemetry coupling member adjacent to an IMD.

FIG. 5 is a schematic diagram illustrating an example delivery catheter 30 having an antenna 32 as the telemetry coupling member. Delivery catheter 30 may correspond with delivery catheter 20 of FIGS. 1, 3 and 4 with antenna 32 corresponding to telemetry coupling member 22. External device 18 is connected to feed line 16 of delivery catheter 30 and sends or receives electrical signals along feed line 16 to or from antenna 32. In the example illustrated in FIG. 5, the feed line 16 comprises a conductor 34 that extends along a length of catheter body 31 from the proximal end of catheter body 31 to the distal end of catheter body 31 adjacent to IMD 36. Conductor 34 is located within an inner lumen defined by catheter body 31. A first portion of conductor 34 forms feed line 16 and a second portion of conductor 34 forms antenna 32. For example, the conductor extends from the proximal end of catheter body 31 to the distal end of catheter body 31 adjacent to IMD 36, forms antenna 32 near the distal end of catheter body 31 and then returns back to the proximal end of catheter body 31.

In the example illustrated in FIG. 5, conductor 34 is connected to external device 18 at a proximal end of catheter body 31. Conductor 34 forms a coil antenna near the distal end of catheter body 31, which functions as the telemetry coupling member 22. In particular, conductor 34 includes one or more turns around a longitudinal axis 38 of delivery catheter 30. The electrical signal sent from telemetry device 18 causes antenna 32 to create an electromagnetic field for coupling to a corresponding antenna (not shown in FIG. 5) within IMD 36. Conductor 34 is exemplary illustrated as feed line 16 and antenna 32 forms a coil antenna in the example of FIG. 5. The conductor may form antennas of any of a variety of different shapes, such as a planar shape (FIG. 8), a cylindrical shape (FIG. 7) or other shape. Moreover, in other instances, feed line 16 and the antenna 32 may be formed from separate conductors and coupled together, e.g., via an electrical connection.

FIGS. 6, 7 and 8 illustrate further examples of delivery catheters with antennas as telemetry coupling members. FIG. 6 illustrates a distal end of a delivery catheter 40 that includes a feed line 16 and antenna 32 which are both contained within the walls of catheter body 41. Antenna 32 of FIG. 6 includes one or more turns around a longitudinal axis 38 of delivery catheter 40. The turns of antenna 32 are within the walls of catheter body 41. In other words, the turns of antenna 32 follow the circumference of catheter body 41. The turns of antenna 32 may at least partially encircle and, in some instances, completely encircle IMD 36 when IMD 36 is located in the distal portion of catheter 40. Construction in this manner allows for a large volume within which the electromagnetic field is sufficient for communicating with IMD 36. As such, the placement of the corresponding antenna within IMD 36 is less critical when the delivery catheter antenna surrounds IMD 36 than in the embodiment in which the delivery catheter antenna is located near one end of IMD 36. Moreover, embedding feed line 16 and antenna 32 in the walls of catheter body 41 may simplify the process for IMD 36 to be delivered from outside patient 10 to inside patient 10 through delivery catheter 40 after delivery catheter 40 is placed at least partially within patient 10. Without the feed line 16 embedded within the walls of catheter body 41, to deliver the IMD 36 from outside the patient 10 to inside the patient 10, requires inserting the telemetry coupling member after inserting the IMD 36 and moving both from the proximal end of delivery catheter to the distal end of delivery catheter.

Although feed line 16 and antenna 32 are illustrated in FIG. 6 as being contained within the catheter body 41, in other instances feed line 16 and/or a portion of antenna 32 may be located within the inner lumen defined by the walls of the catheter body. For example, feed line 16 may be located within the inner lumen defined by the walls of the catheter body and may couple to antenna 32 which may be located within the walls of the catheter body or vice versa.

FIG. 7 illustrates a distal end of another example delivery catheter 44 in which antenna 32 encircles at least a portion of IMD 36 at or near the distal end of delivery catheter 44. In the example of FIG. 7, feed line 16 and antenna 32 are within the lumen of delivery catheter 44 (similar to the embodiment of FIG. 5), but antenna 32 encircles at least a portion of IMD 36 and, in some instances, completely encircles IMD 36.

FIG. 8 illustrates a distal end of another example delivery catheter 46 that includes an antenna 48 which forms a planar surface. The planar surface formed by antenna 48 is normal to the longitudinal axis 38 of delivery catheter 46 and antenna 48 is adjacent to IMD 36, similar to antenna 32 of catheter 30 of FIG. 5.

Figure 9:
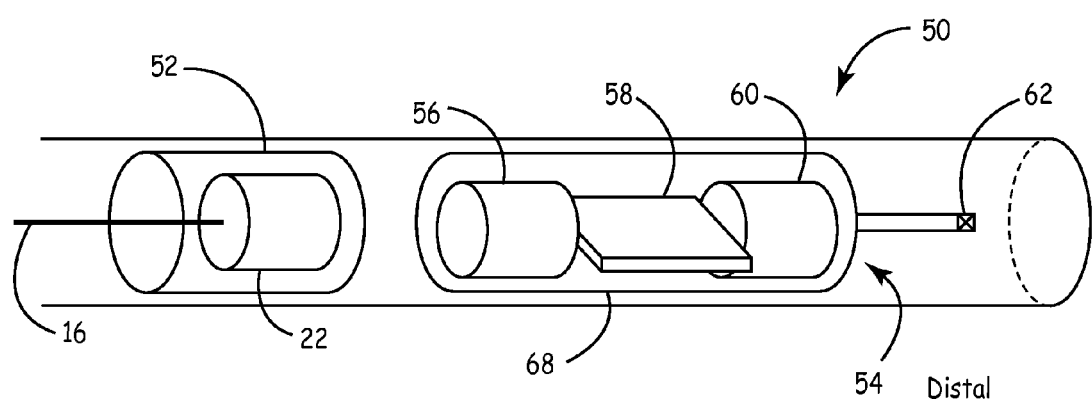
FIG. 9 is a conceptual diagram illustrating an example catheter, a delivery module and an IMD.

FIG. 9 is a conceptual diagram illustrating a distal end of an example delivery catheter 50 in further detail. Delivery catheter 50 may correspond with any one of delivery catheters 20, 30, 40, 44 or 46 or other delivery catheter. Delivery catheter 50 includes a delivery module 52 to deliver an IMD 54 to the target location within patient 10. In the example illustrated in FIG. 9, delivery module 52 of delivery catheter 50 contains a telemetry coupling member 22 and is connected to feed line 16. Feed line 16 may be a wire or pair of wires used for the bi-directional transmission of signals between external device 18 and IMD 54. However, the transmission may also be unidirectional, either from external device 18 to IMD 54 or from IMD 54 to telemetry device 18.

IMD 54 is shown conceptually in the right hand portion of FIG. 9. IMD 54 may correspond to either IMD 14 or 36, or other IMD described herein. IMD 54 includes an IMD telemetry coupling member 56, circuit 58, power source 60 and electrode 62. IMD telemetry coupling member 56 may be similar to telemetry coupling member 22 of delivery catheter 20, e.g., an antenna, a transducer, an electrical contact, a capacitive plate, an electrode or the like. IMD telemetry coupling member 56 is located adjacent to the delivery module 52 in the illustrated example. In instances in which telemetry coupling members 22 and 56 are antennas, the antennas may be formed in a similar manner, e.g., from a coil with one or more turns around a longitudinal axis 38 of delivery catheter 50, or may be formed in different manners. IMD telemetry coupling member 56 and telemetry coupling member 22 of delivery module 52 are arranged with respect to one another in a manner to provide an effective communicative coupling, e.g., electromagnetic, inductive, RF coupling or the like. In one example, IMD telemetry coupling member 56 is an antenna wound around the longitudinal axis of delivery catheter 50 or has windings with other orientations to facilitate construction or communications with other devices or for other reasons.

IMD telemetry coupling member 56 connects to circuit 58. Circuit 58 may include functional electronics (modules and/or components) for the functions performed by IMD 54, including sensing, therapy, telemetry, programming, testing, measuring, battery monitoring or the like. Power source 60 connects to circuit 58 to provide power during the service life of IMD 54. Power source 58 may, for example, comprise a rechargeable or non-rechargeable battery.

IMD 54 includes a capsule 68 and an electrode 62. IMD 54 is implanted such that electrode 62 is lodged within viable tissue of the target location for the purposes of stimulating the tissue, sensing a parameter from the tissue and in some embodiments, conductively coupling to the tissue for the telemetry communication. In the example illustrated in FIG. 9, IMD 54 is a capsule 68 of cylindrical shape. However, the techniques of this disclosure are not limited to cylindrical shapes. Capsule 68 may, in other instances, take on any of a variety of shapes. Capsule 68 is built to fit within the lumen of delivery catheter 50 and accommodate battery 60 or components/circuits to harvest power from internal or external sources, circuit 58, and IMD telemetry coupling member 56. While capsule 68 is long enough to encapsulate the aforementioned components, capsule 68 is not so long as to inhibit movement through the delivery catheter 50, especially if delivery catheter 50 is to be placed before IMD 54 is received into delivery catheter 50. The length of the capsule 68 may be limited to accommodate delivery through the path taken by the delivery catheter 50 to reach the target implantation site. The dimensions of capsule 68 may also be limited by the size and structures of the target organ.

Electrode 62 extends from capsule 68 to deliver therapy to, to sense a parameter from the target location and, in some embodiments, to conductively couple to a tissue for the telemetry communication. Electrode 62 may be lodged within a tissue at the target location or located adjacent to the target location. In the case of an implantable pacemaker, for example, electrode 62 may be lodged within tissue of a heart chamber to deliver pacing pulses to the chamber of the heart or sense depolarizations of the chamber of the heart. IMD 54 of FIG. 9 is illustrated for exemplary purposes and should not be considered limiting of the techniques as described herein. In other examples, electrode 62 may not extend from capsule 68. Instead or in addition, some or the entire exterior of capsule 68 may be formed from a conductive material that may function as the electrode. In further examples, IMD 54 may include more than one electrode. In other instances, IMD 54 may not provide electrical stimulation therapy and, therefore, not include an electrode at all. Instead, IMD 54 may include some other type of sensor, such as a glucose sensor, pH sensor, pressure sensor, accelerometer, or any other sensor, to measure a parameter of patient 10.

IMD 54 may further include a fixation mechanism (not shown) to affix IMD 54 to the target location. The fixation mechanism may include sutures that are sutured to the target location, flexible tines that protrude into the target location, helical mechanisms that are screwed into the target location, a stent for retention in a vessel or the like. In some instances, at least a portion of electrode 62 may be shaped to form the fixation mechanism. In other words, electrode 62 is the fixation mechanism. For example, at least a portion of electrode 62 may be shaped into a helical structure to screw into the target location to affix IMD 54 as well as deliver therapy to or sense a parameter of the target location. As described above, delivery catheter 50 may include one or more pull wires or other means for manipulating the position of IMD 54 to move IMD 54 within catheter body or to affix (e.g., via turning) IMD 54 to the target location.

The delivery catheter 50 may also include an attachment mechanism for detachably coupling to IMD 54. The attachment mechanism may be used to push, pull, rotate or otherwise manipulate the position of IMD 54 within delivery catheter 50. As one example, the attachment mechanism may be used to push IMD 54 to the distal end of delivery catheter 50, rotate IMD 54 to affix IMD 54 to the target location and then release IMD 54 from delivery catheter 50. In this manner, IMD 54 is expelled through the distal end of delivery catheter 50 and placed within the target location. In the example illustrated in FIG. 9, feed line 16 may also function as the mechanism to manipulate the position of IMD 54, e.g., using delivery module 52, in addition to functioning as the feed line.

Prior to expulsion of IMD 54 from delivery catheter 50, it may be desirable to determine whether IMD 54 is located in a suitable location such that IMD 54 will function as desired or intended and is not detrimental to the function of the target organ or other location. As such, it may be desirable to perform one or more tests prior to expulsion of IMD 54 from delivery catheter 50 to ensure these functional expectations will be met during the service life of IMD 54 or to gain confidence that IMD 54 will remain in the desired position. In the example of the IMD as a cardiac pacemaker system, it may be desirable to measure the performance of electrode 62. Such testing might include measurement of the stimulation threshold, the impedance of the electrode-tissue interface as presented to IMD 54, the amplitude of sensed electrogram potentials from appropriate chambers of the heart, the amplitude of sensed electrogram potentials from other chambers of the heart, the appropriate detection of various physiologic sensors within IMD 54, the hemodynamic consequences of pacing (e.g. cardiac output when paced from the selected location), the communicative coupling to IMD 54 or between IMD 54 and other devices implanted or to be implanted within the patient, any hemodynamic obstruction that may be caused by the IMD 54 as located in the heart, and the security of the fixation (e.g., applying tension to the IMD to determine whether the fixation mechanism has sufficiently engaged the appropriate surrounding tissue).

IMD 54 may perform the one or more tests in response to a communication signal from external device 18. In this manner, external device 18 controls IMD 54 to perform the one or more tests. After performing the one or more tests, IMD 54 sends a communication signal back to external device 18 that includes the results of the performed tests. The results provided to external device 18 may be raw sensor data that may be processed by external device 18 to determine the suitability of attachment of IMD 54 to the target location. Alternatively, IMD 54 may process the data and provide an indication of the suitability of the attachment of IMD 54 to the target location via the communication signal. External device 18 may present the results to a user via display module 29 or other output.

Figure 10A:
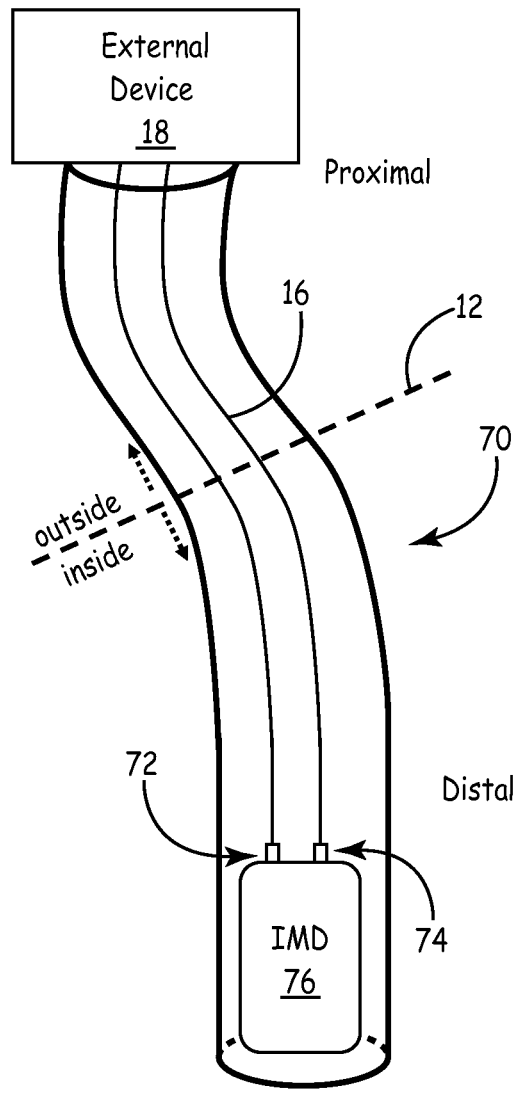
FIG. 10a is a schematic diagram illustrating an example delivery catheter with direct electrical connections.

FIG. 10*a* is a schematic diagram illustrating an example delivery catheter 70 that includes electrical connectors 72, 74 that connect directly to IMD 76. Catheter 70 may correspond with catheter 20 of FIGS. 1, 3 and 4 and IMD 76 may correspond with IMD 14. The telemetry coupling member of delivery catheter 70 comprises electrical connectors 72, 74 and the communicative coupling is an electrical coupling. Electrical connections 72, 74 allow signals from telemetry device 18 to flow directly to the telemetry circuitry within IMD 76. By virtue of using a direct electrical connection for the telemetry of information between external device 18 and IMD 76, communication is extremely reliable, noise-free and may require less energy as compared to wireless methods. When IMD 76 has been navigated to an appropriate position, fixed to the target location and expelled from delivery catheter 70, IMD 76 is disconnected from the feed line 16 and communicates with external device 25 (see FIG. 3) via wireless communication.

Figure 10B:
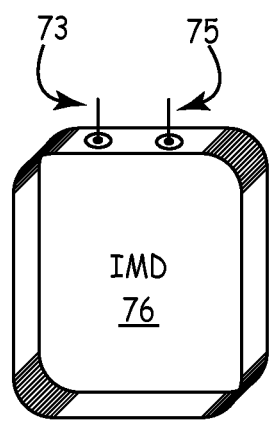

FIG. 10*b* provides an example detail view of IMD 76 with detachable electrical connectors 73, 75. Electrical conductors may be routed though insulative structures in the housing of IMD 76 to form electrical connectors 73 and 75. The electrical conductors extending through insulative structures in the housing of IMD 76 may electrically couple to one or more components within IMD 76, such as a power source (FIG. 9 reference numeral 60, FIG. 21 reference number 144) or circuitry (e.g., a telemetry module) within IMD 76. Connector mechanisms may be provided to detachably connect feed line 16 to IMD 76 and then disconnect prior to delivery of IMD 76 to the target location. In other words, the connector mechanisms connect electrical connects 73, 75 to electrical connectors 72, 74. Besides the communicative coupling mechanism, IMD 76 functions in a similar manner to IMDs 14, 36 to provide therapy to and/or monitor a parameter of patient 10.

Figure 11A:
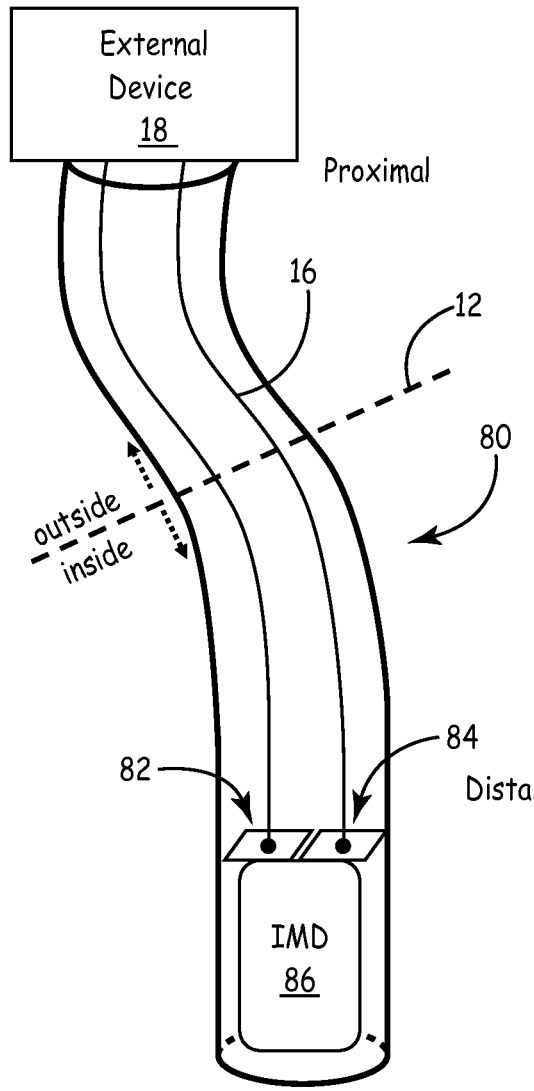
FIG. 11a is a conceptual diagram illustrating an example delivery catheter with a capacitive connection between a feed line and an IMD in the distal end of a catheter.
Figure 11B:
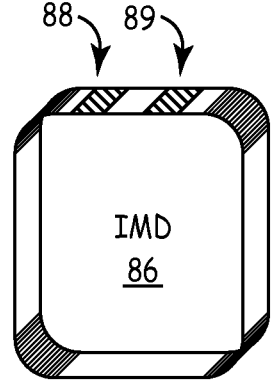

FIG. 11*a* is a schematic diagram illustrating an example delivery catheter 80 that includes capacitive plates 82, 84 that communicatively couple to IMD 86. Catheter 70 may correspond with catheter 20 of FIGS. 1, 3 and 4. The telemetry coupling member of delivery catheter 80 comprises capacitive plates 82, 84 and the communicative coupling is a capacitive coupling. Capacitive plates 82, 84 are located at the distal end of feed line 16 and align with the complementary IMD plates 88, 89 (FIG. 11*b*) on IMD 86.

Capacitive plate 82 and IMD plate 88 are parallel plates or nearly parallel plates with blood or other body fluid as a dielectric. In this configuration plate 82 and plate 88 form a capacitor. Similarly, capacitive plate 84 and the IMD plate 89 form another capacitor. Through these capacitive connections, telemetry device 18 and IMD 86 exchange telemetry signals without direct electrical connection. Besides the communicative coupling mechanism, IMD 86 functions in a similar manner to IMDs 14, 36 to provide therapy to and/or monitor a parameter of patient 10.

Figure 12:
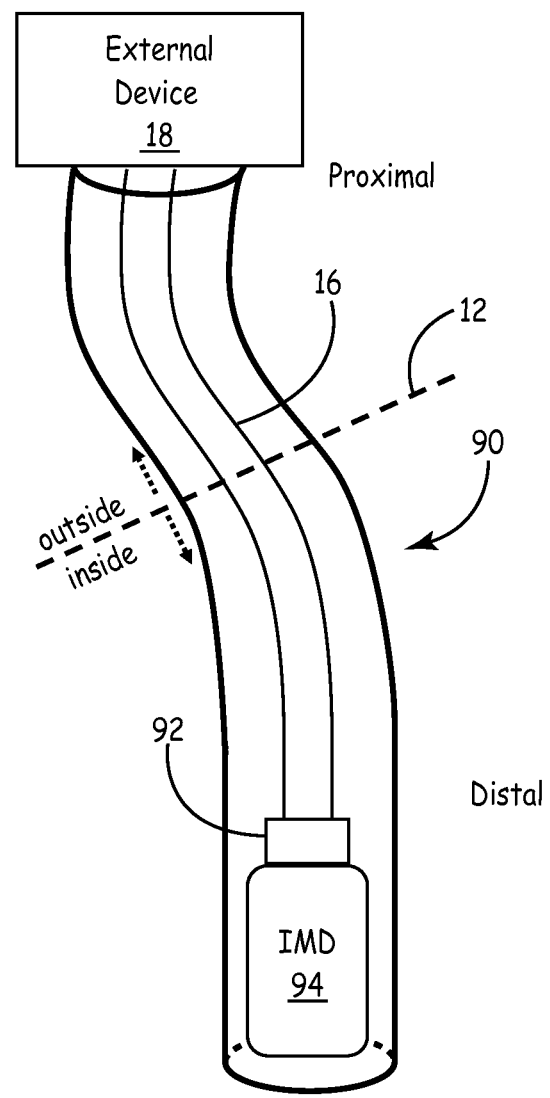
FIG. 12 is a conceptual diagram illustrating an example delivery catheter with a transducer.

FIG. 12 is a schematic diagram illustrating an example delivery catheter 90 that includes a transducer 92 that communicatively couples to IMD 94. Catheter 90 may correspond with catheter 20 of FIGS. 1, 3 and 4. The telemetry coupling member of delivery catheter 90 is transducer 92 and the communicative coupling is a mechanical, electromechanical, acoustic, electroacoustic, optical or electro-optic coupling. At the distal end of feed line 16, an electrical connection from feed line 16 is made to transducer 92. Transducer 92 converts electrical signals from the feed line to nonelectrical signals. The nonelectrical signals may, for example, be vibration, sound or other nonelectrical signal. The mechanical connection between delivery system transducer 92 and a corresponding transducer within IMD 94 is maintained either through direct mechanical contact, mechanical linkage, through contact with delivery catheter 90 or through fluidic means such as through blood, other body fluid, saline or the like. The corresponding transducer (not shown) is located within IMD 94 to receive and send the communication from IMD 94. Besides the communicative coupling mechanism, IMD 90 functions in a similar manner to IMDs 14, 36 to provide therapy to and/or monitor a parameter of patient 10.

Figure 13:
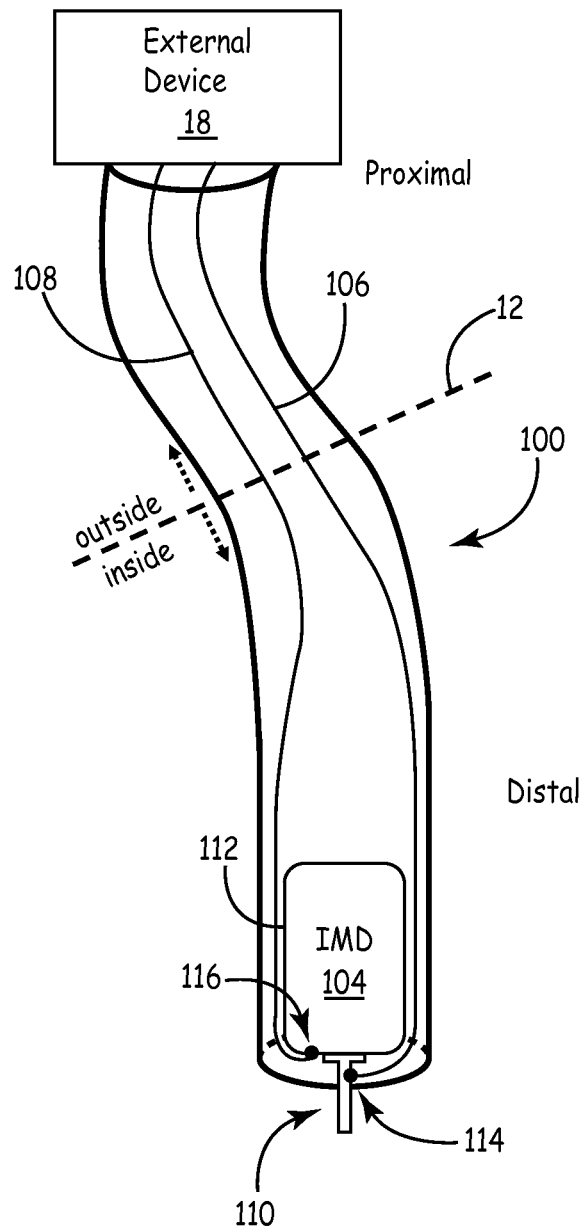
FIG. 13 is a schematic diagram illustrating an example IMD connected to an external device.

FIG. 13 is a schematic diagram of a delivery catheter 100 coupled to external device 18. External device 18 incorporates analyzer module 27 (see FIG. 2) to test the suitability of IMD 104 to perform its desired functions. Analyzer module 27, however, may be constructed as a stand alone instrument or in combination with other external instrumentation such as external device 18, a programming device, a physiologic monitoring system, an imaging system or a navigation system. Delivery catheter 100 includes conductors 106 and 108 that serve to connect external device 18 to one or more electrodes of IMD 104. In other words, conductors 106 and 108 may be viewed as control lines or feed lines that carry electrode signals to and from electrode 110, e.g., for testing the suitability of the implant location. Conductors 106 and 108 may also be employed to translate mechanical forces from the proximal end to the distal end of the delivery catheter for use in moving or manipulating the position of IMD 104, in addition to serving in electrical roles such as to carry telemetry signals to and from the IMD and/or to carry signals to and from an electrode 110. In the example illustrated in FIG. 13, conductor 106 detachably connects external device 18 to electrode 110 of IMD 104 through the electrode connection 114 and conductor 108 detachably connects external device 18 to a capsule 112 of IMD 104 via capsule connection 116.

Capsule 112 of IMD 104 may be made from a conductive material, such as of titanium, or from a non-conductive material, such as ceramic. In the example of a conductive capsule, the connection from the electronic circuitry inside capsule 112 to electrode 110 comprises an insulator and a seal such that a central conductor passes through capsule 112 of IMD 104 while being electrically insulated from capsule 112. Capsule 112, if conductive, may be used as another electrode, either using the whole of capsule 112 or in part. To be used in part, capsule 112 may be coated, in part, with an insulative coating such as paralene, the remaining uncoated portion serving as the another electrode. In the example of an insulative capsule, the connection to electrode 110 comprises a seal such that the central conductor passes through capsule 112 of IMD 104 but further insulation may not be necessary. In both examples, mechanical support such as strain relief may be integrated into the seal.

External device 18 may test the electrical suitability of capsule 112 and electrode 110 of IMD 104 to perform the necessary functions of IMD 104. In the example of a cardiac rhythm management device, these functions may include stimulating the heart, sensing depolarizations of the heart, presenting a suitable impedance to IMD 104 and telemetry communication. Other functions may be tested for other types of IMDs, e.g. neurostimulators, drug pumps or the like, in addition to or instead of the functions described above. After testing the suitability of IMD 104 to perform its desired function, conductors 106 and 108 can be disconnected or detached from the respective connections 114 and 116 to enable IMD 104 to be released from delivery catheter 100. Additionally, IMD 104 may be turned on or powered up in response to the testing indicating desired functionality. Power is conserved by having external device 18 perform the suitability testing instead of IMD 104.

The position and orientation of an electrode or electrodes on an IMD may be important for embodiments utilizing conductively coupled communication through the body as the communication signal generated by the IMD may be weak. Little power can be budgeted for telemetry communication as the power source within the IMD must be small to fit within the IMD and to power the circuitry for its therapeutic, monitoring and telemetric communication purposes for a reasonable service life. Delivery by catheter enables placement of the IMD deep within the body. For large patients and especially for obese patients, the depth of IMD placement may result in a long distance between the body electrodes on the surface of the patient and the electrodes used for telemetry on the IMD. This long distance may result in especially small signals on the body surface. Clinical follow-up and care of patients with IMD's generally follows a standard practice such as affixing electrodes to the patient for monitoring during such sessions. Such procedures demand to be done in a minimum of time with little to no experimentation in the setup of the system. Therefore, it is desired the body electrodes be affixed to the patient in a standard position such as on the patient's wrists, on the patient's chest or some familiar anatomical location. Locations that can be accessed without the need for the patient to disrobe are, further, preferred. With a fixed and standard location for body electrodes for telemetric communication with the IMD, some positions and associated orientations of the IMD may work better than others.

Figure 14:
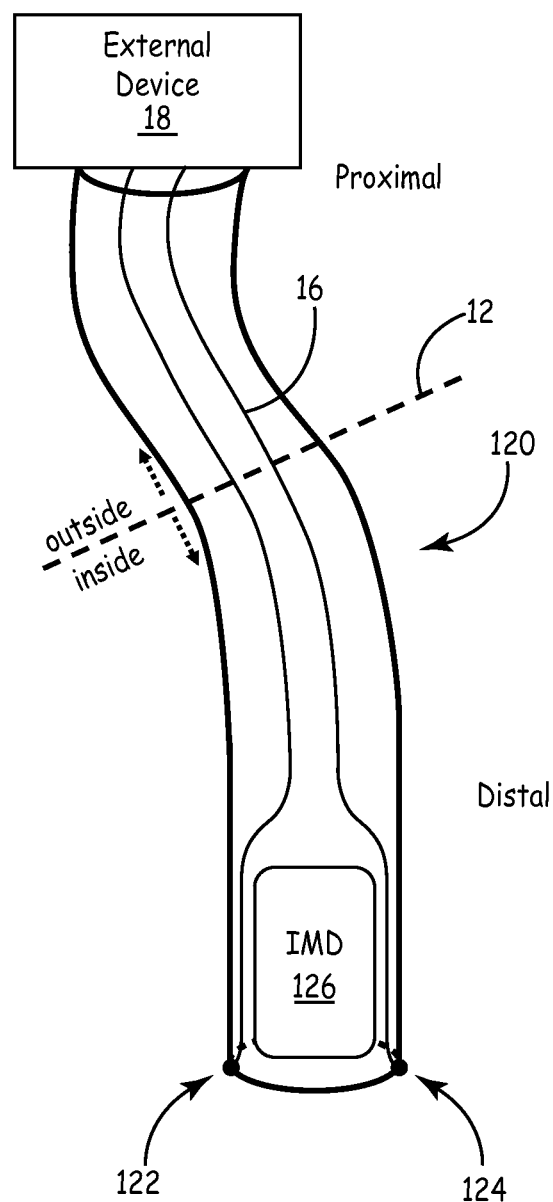
FIG. 14 is a schematic diagram illustrating an example catheter having telemetry coupling electrodes.

FIG. 14 is a schematic diagram of a delivery catheter 120 which communicates using conductive coupling. Delivery catheter 120 includes a feed line 16 coupled to telemetry coupling electrodes 122, 124 on (e.g., at or near) the distal end of catheter 120. External device 18 is coupled to the feed line 16 at the proximal end of catheter 120. External device 18 generates and receives a communication signal through the telemetry coupling electrodes 122, 124 which are inside the body of patient 10 using the body as a conductor, a process sometimes referred to as tissue conductance communication (TCC). Such a communication technique is described in detail in U.S. Pat. No. 4,987,897 to Funke entitled, "BODY BUS MEDICAL DEVICE COMMUNICATION SYSTEM" filed Sep. 18, 1989, which is incorporated by reference herein in its entirety.

Telemetry coupling electrodes 122, 124 may be placed on catheter 120 to approximate the spacing of telemetry electrodes on IMD 126. In this manner, testing conductively coupled communication with telemetry coupling electrodes 122, 124 will mimic the telemetry electrodes on IMD 126. For example, IMD 126 may include telemetry electrodes on opposite ends of IMD 126 (e.g., a proximal and distal end of IMD 126 corresponding to the proximal and distal references of catheter 120 while IMD 126 is resident in catheter 120) and telemetry coupling electrode 122 may be located at the distal end of catheter 120 to approximate an electrode at the distal end of IMD 126 and telemetry coupling electrode 124 may be located slightly proximal from the distal end of the catheter body to approximate an electrode located at the proximal end of IMD 126. Other configurations of telemetry coupling electrodes 122, 124 may be utilized to approximate the location of telemetry coupling electrodes of IMD 126. In this manner, telemetry coupling electrodes may provide an accurate indication as to telemetry performance after IMD 126 is implanted.

Telemetry coupling electrodes 122, 124 may take on a variety of shapes and sizes such as a ring or a band around the circumference of elongate catheter 120 or they could be other shapes which do not encircle the catheter. The telemetry coupling electrodes 122, 124 could extend through the wall of catheter 120 to provide contact with blood or body fluid or saline or the like within catheter 120 as well as being exposed to blood or body fluid on the outside of catheter 120.

Figure 14A:
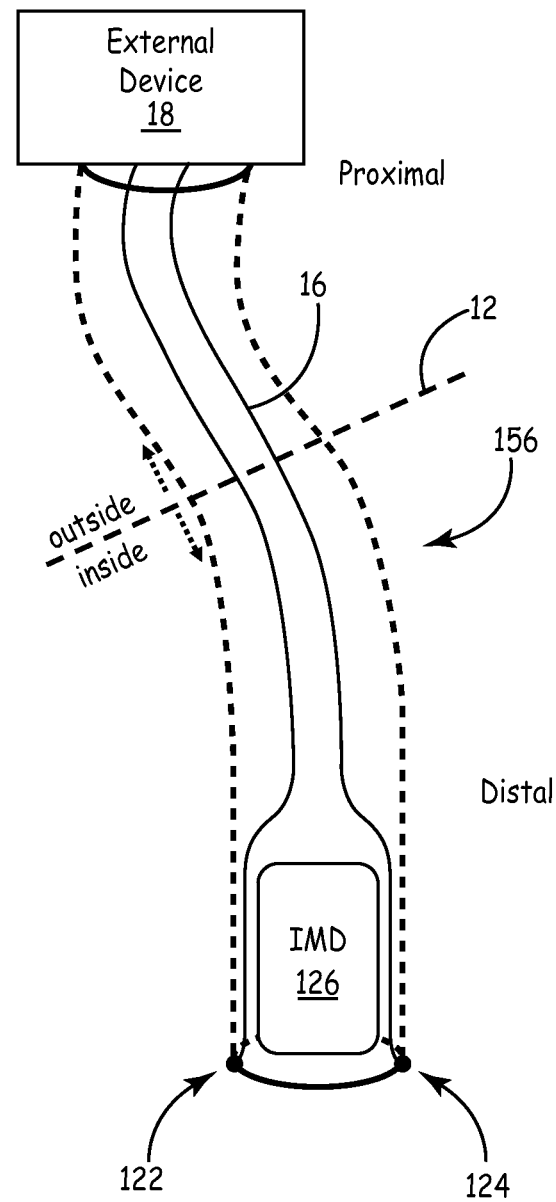
FIG. 14a is a schematic diagram illustrating another example catheter having telemetry coupling electrodes.

FIG. 14a is a schematic diagram of a delivery catheter 156 which communicates using conductive coupling. Delivery catheter 156 substantially conforms to delivery catheter 120 of FIG. 14, but delivery catheter 156 incorporates one or more holes in the catheter wall to allow the ingress of blood and conductively coupled communication between IMD 126 and a body electrode (described below). In other words, the delivery catheter body may be formed in such a manner as to create the voids or holes. The holes in delivery catheter 156 are placed so as to provide electrical coupling through the ingress of blood to the central lumen of catheter 156 and to retain the strength and maneuverability necessary for navigation and delivery of IMD 126 within the patient 10.

While FIG. 14a illustrates the holes in catheter 156 as extending from the proximal end to the distal end, the holes may be placed only in certain portions of catheter 156. For example, the holes might be placed only in the distal portion of catheter 156 such that they expose IMD 126 to the blood when IMD 126 is placed in the distal portion of catheter 156 for navigation, testing and delivery. In another embodiment, the hole placement includes the use of holes only in the distal portion of catheter 156 and only in the area around a proximal telemetry electrode (not shown) on IMD 126 where the proximal telemetry electrode may be a distinct telemetry electrode member or may be an uninsulated portion of the capsule. In yet another embodiment, holes may extend along the length of catheter 156 that will indwell within patient 10. That is, the holes would extend from the site 12 of entry into patient 10 to the distal end of catheter 156 so conductive communication with IMD 126 could be established as IMD 126 is passed through catheter 156 during a procedure in which catheter 156 is first introduced into patient 10 and then IMD 126 is placed in the distal end of catheter 156.

Figure 15:
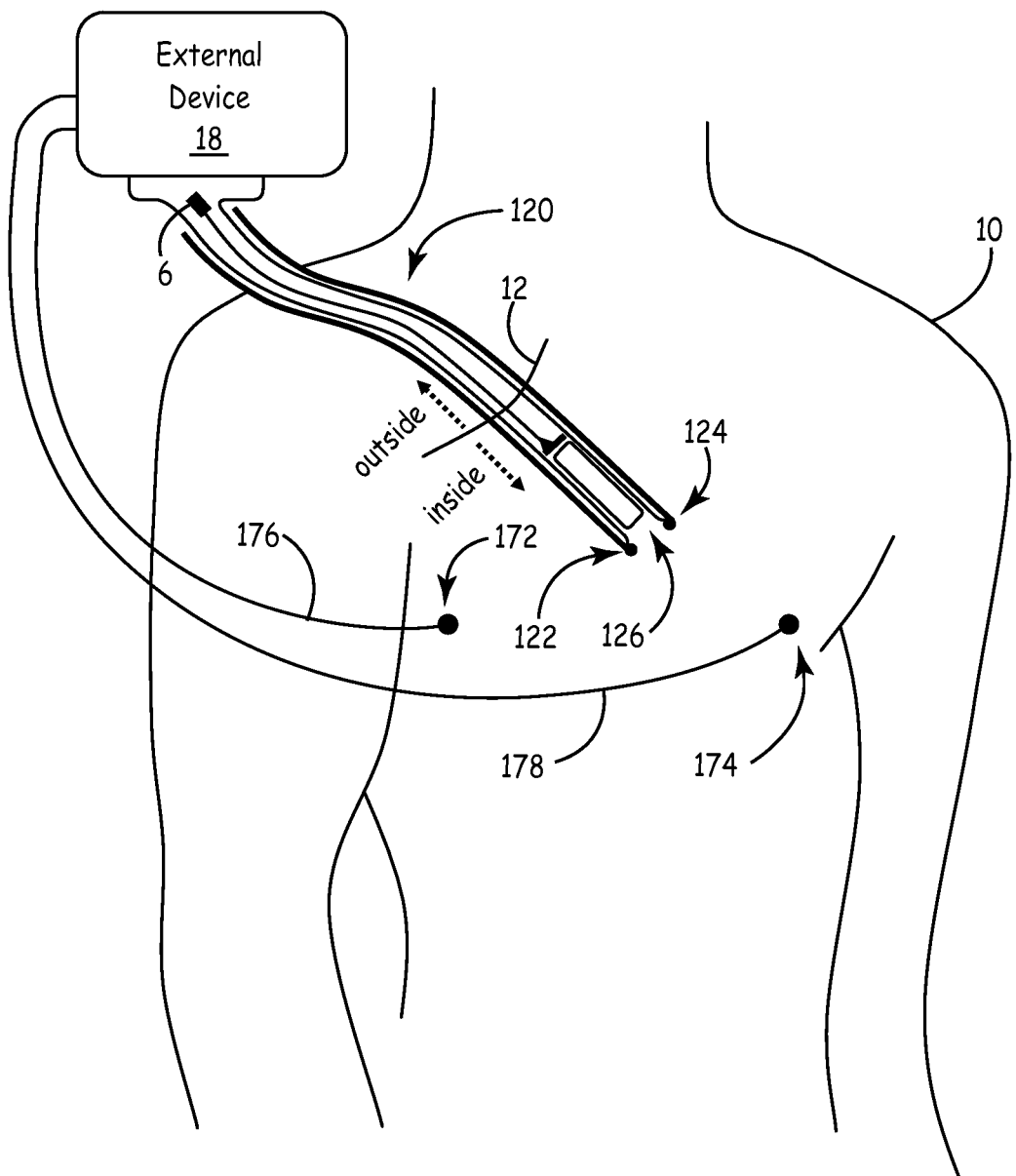
FIG. 15 is a schematic diagram illustrating an example delivery system utilizing body electrodes on a patient.

FIG. 15 illustrates the delivery system of FIG. 14 indwelling in patient 10. The external device 18 is coupled to body electrodes 172, 174 via body electrode cables 176, 178. The external device 18 assesses the communication between the indwelling electrodes 122, 124 and electrodes which are on the body surface, body electrodes 172, 174 in the example illustrated in FIG. 15 using conductive coupling (e.g., TCC). The external device 18 may communicate with the IMD 126 by use of the telemetry coupling electrodes 122, 124. For example, telemetry coupling electrodes 122, 124, which are electrically coupled to external device 18, may be conductively coupled to corresponding electrodes (not shown in FIG. 15) on IMD 126. Further, the external device 18 may direct the IMD 126 to communicate with the body electrodes 172, 174 via conductive coupling.

To assess the communication, the external device 18 may transmit a communication signal from the body electrodes 172, 174 and measure the received communication signal at the IMD 126 and/or the telemetry coupling electrodes 122, 124. The communication may also be in the opposite direction. The IMD 126 may transmit a communication signal and the external device may then receive the signal from the body electrodes 172, 174. In a third mode of communication, the external device 18 transmits a communication signal from the telemetry coupling electrodes 122, 124 and the signal is then received by the body electrodes 172, 174.

The IMD 126 or the external device 18 may measure the quality of the communication signal to assess the viability of communication between the IMD 126 and the body electrodes 172, 174. In the communication assessments in which IMD 126 is involved (e.g., either as the transmitting or receiving device), the quality of the communication between IMD 126 and the body electrodes 172, 174 is directly determined. In the communication assessments in which IMD 126 is not involved (e.g., the signals are transmitted between body electrodes 172, 174 and telemetry coupling electrodes 122, 124), the quality of the communication signal between IMD 126 and the body electrodes 172, 174 is being approximated since the location of telemetry coupling electrodes 122, 124 are located in close proximity to the eventual position following implantation of the electrodes on IMD 126 that will be used for communication. The quality of the communication signal may be assessed by a variety of methods including but not limited to a transmission power required for signal detection, a received signal strength, a received signal to noise ratio, a bit error rate, a data throughput rate, a data dropout rate, a background noise floor, an optimum frequency, an optimum set of electrodes in IMD 126, or a combination of these measurements. The IMD 126 and the external device 18 may communicate and select from a variety of appropriate communication frequencies. Certain communication frequencies may be selected to avoid interfering signals from other devices such as other IMDs or the like. The IMD 126 and the external device 18 may synchronize the sequential testing of the variety of communication frequencies and then select the communication frequency which is determined to be optimal for reliable communication. The IMD 126 may incorporate a series of electrodes (not shown) from which the IMD 126 may select or be directed by external device 18 to select the electrodes for telemetry communication. The IMD 126 can sequentially select from among the series of electrodes to test and select the electrode which is determined to be optimal for reliable communication. The communication signal path through the body may be assumed to be the same in both directions so only one direction need be tested or it may be tested in both directions.

The external device 18 reports the communication signal quality in an electronic format, in a printed format, or by visual display via the display module 29. The report contains any of the measurements of the communication signal quality and may contain these measurements as a function of time. The various measurements may be combined into a simplified quantitative index of the communication signal quality so the user need not be concerned with the technical details of the communication but only with whether the communication signal quality is satisfactory for long-term use with IMD 126.

Figure 16:
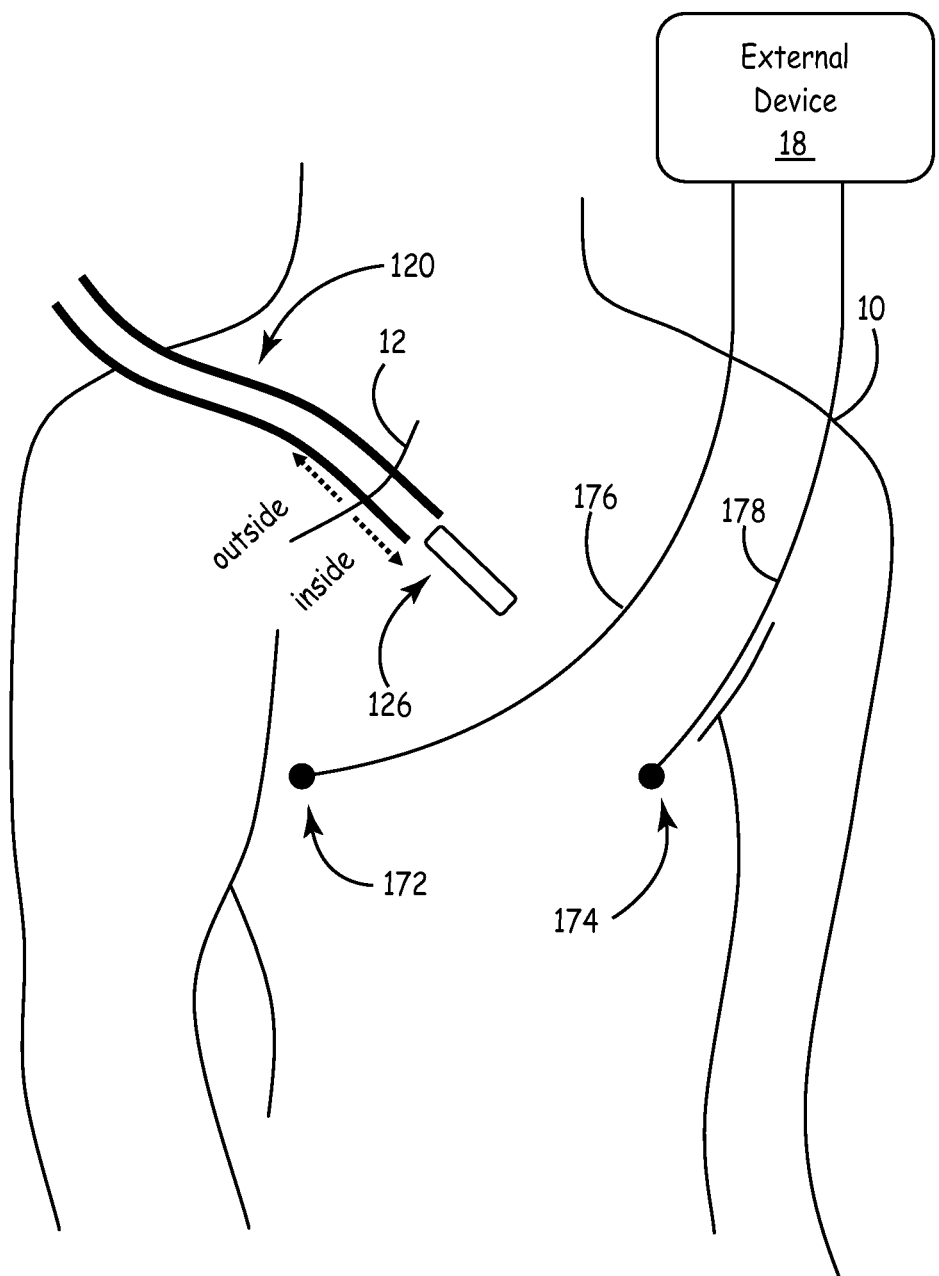
FIG. 16 is a schematic diagram illustrating the example delivery system of FIG. 15 within IMD expelled from a delivery system catheter.

Assessment of the communication signal quality is useful to guide placement of the IMD 126. If, once implanted, as illustrated in FIG. 16, the IMD 126 placement is not expected to result in reliable and useful communication between the IMD 126 and the external device 18, implantation may be ill-advised for lack of communication could render the device not useful or might require subsequent extraction. If the IMD 126 is placed in position for implantation but still within and/or attached to the delivery catheter, the communication signal quality can be tested. Referring back to FIG. 15, the external device 18 utilizes the communication signal quality measurements to predict whether the communication between the IMD 126 and the external device 18 will be successful after the implantation assuming the orientation and position of the IMD 126 are not substantially changed from the position during which testing of the communication signal quality is performed. The IMD 126 may be placed such that the electrode on the IMD 126 which may be used for therapeutic or monitoring purposes but is also used for conductively coupled communication through the body is essentially fully lodged and implanted but not detached from the delivery system. In this position, testing the communication signal quality between the telemetry electrodes of IMD 126 or telemetry coupling electrodes 122, 124 and the body electrodes 172, 174 provides the external device 18 sufficient information for the external device 18 to predict whether communication between the IMD 126, after implantation, and the external device 18 will be satisfactory.

Figure 17:
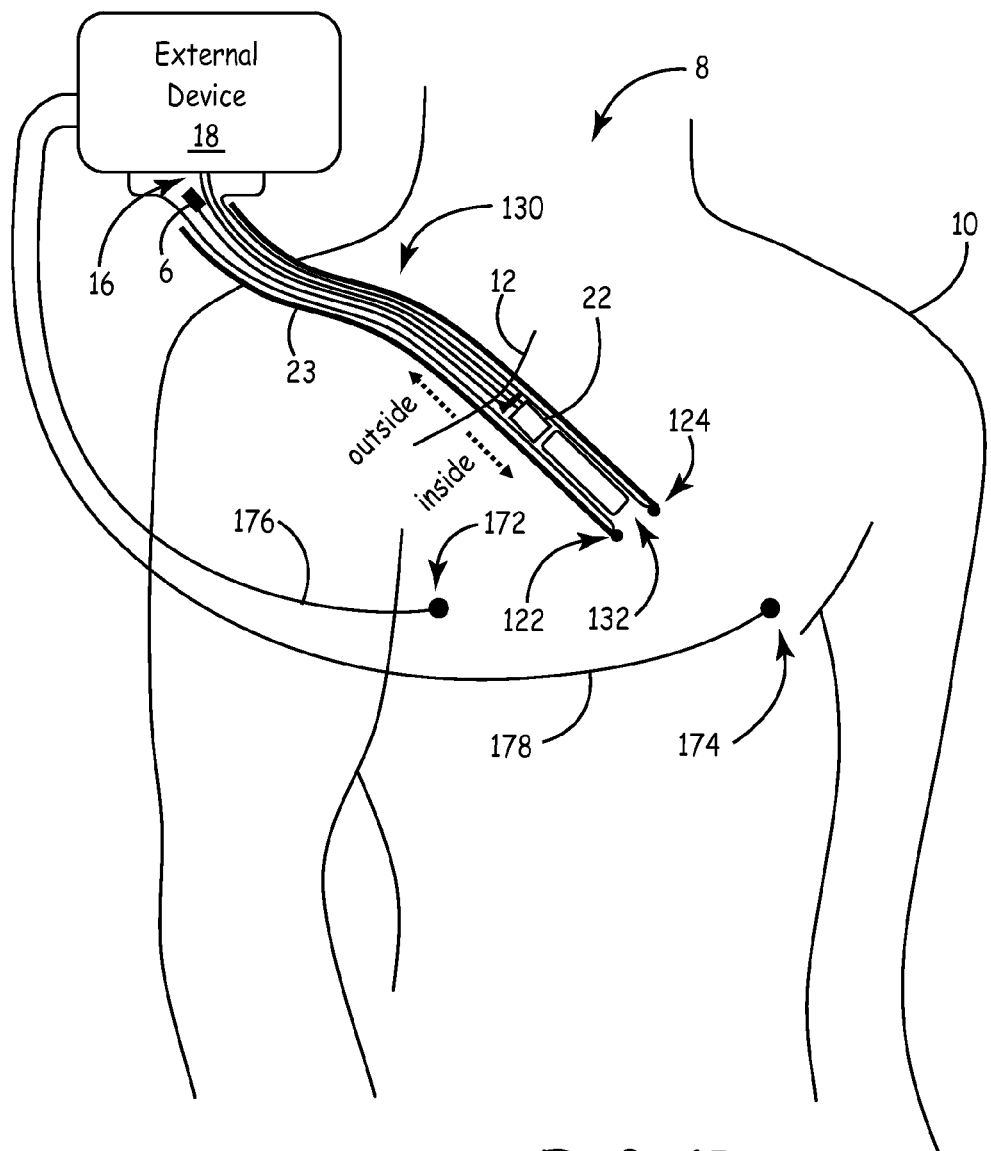
FIG. 17 is a schematic diagram illustrating an example delivery system catheter having a telemetry coupling member and telemetry coupling electrodes.

Various embodiments may be combined in the IMD delivery system. FIG. 17 illustrates an embodiment wherein the delivery system catheter comprises both telemetry coupling electrodes 122, 124 and telemetry coupling member 22. In this embodiment, telemetry signal communication with IMD 132 may be accomplished by the various methods attributed above to the telemetry coupling member as well as the conductive coupling using telemetry coupling electrodes 122, 124. IMD 132 may correspond to IMD 126 of FIGS. 14, 15 and 16. Further, the telemetry coupling electrodes 122, 124 have utility in determining the orientation and position of the distal catheter end as described below.

Referring back to FIG. 16, if the communication signal quality between the body electrodes 172, 174 and the IMD 126 is weak or is reported to be unsatisfactory, an alternative for the medical procedure is to reposition the body electrodes 172, 174. The communication signaling with the IMD 126 may be successful with a special position of the body electrodes 172, 174. As the IMD 126 is small, the distance between electrodes on the IMD 126 which are used for conductively coupled communication must, by necessity, also be small. Consequently, the dipole used for generation and reception of conductively coupled communications signals will be small and directional. By attaching a plurality of electrodes 180, 182, 184, 186, 188, 190 to the body (see FIG. 18) and measuring the communication signal quality with each of the electrodes, a variety of body electrode positions can be evaluated so the external device 18 can then report the results. The plurality of electrodes 180, 182, 184, 186, 188, 190 may be coupled to external device 18 via cables 240, 242, 244, 246, 248, 250, respectively. Further, the external device 18 can then recommend a position for the body electrodes 172, 174 (see FIG. 17) for successful communication between the body electrodes 172, 174 and the IMD 126 (FIG. 17).

The above describes finding suitable positions for the body electrodes given the IMD has or will be implanted in a certain position and orientation. An alternative method provides the user with performance measures as a function of various positions and orientations of the IMD. As the user manipulates the delivery system catheter 130 to explore possible implantation sites, the external device 18 records and then reports communication performance as a function of potential IMD site and orientation. The position and orientation for implantation may be determined by various methods. Some example methods for determining position and orientation information are described in U.S. Pat. No. 5,697,377, to Wittkampf entitled, "CATHETER MAPPING SYSTEM AND METHOD," which was filed Nov. 22, 1995 and U.S. Pat. No. 5,983,126 to Wittkampf entitled, "CATHETER LOCATION SYSTEM AND METHOD," which was filed Aug. 1, 1997, both of which are incorporated herein by reference in their entirety. These methods include a three-dimensional measurement of positions within a patient, comprising applying respective three-dimensional orthogonal alternating current signals at respective different frequencies, corresponding substantially to x, y and z directions through said patient, inserting a catheter into said patient, said catheter having a mapping electrode and at least one other electrode and outputting position data representative of such obtained three-dimensional x, y, and z positions. However, other techniques for determining position and orientation for implantation may also be used.

The plurality of electrodes 180, 182, 184, 186, 188, 190 may be utilized for catheter location mapping as with the LOCALISA™ intracardiac tracking system sold by Medtronic, Inc. having a place of business in Minneapolis, Minn. Such a system can localize the position and orientation of the telemetry coupling electrodes 122, 124 on the delivery system catheter 130 or the telemetry electrodes of IMD 132. Alternative localization techniques may be used including electromagnetic localization such as the AXIEM™ electromagnetic tracking system sold by Medtronic Navigation, Inc. having a place of business in Louisville, Colo. An electromagnetic tracking system can localize sensors in the indwelling objects yielding position and orientation of the delivery system catheter 130 and, therefore, the telemetry coupling electrodes 122, 124 and the IMD 132 while coupled to the delivery system catheter 130. The position sensor may be located on (e.g., at or near a distal end) of the catheter 130.

Figure 18:
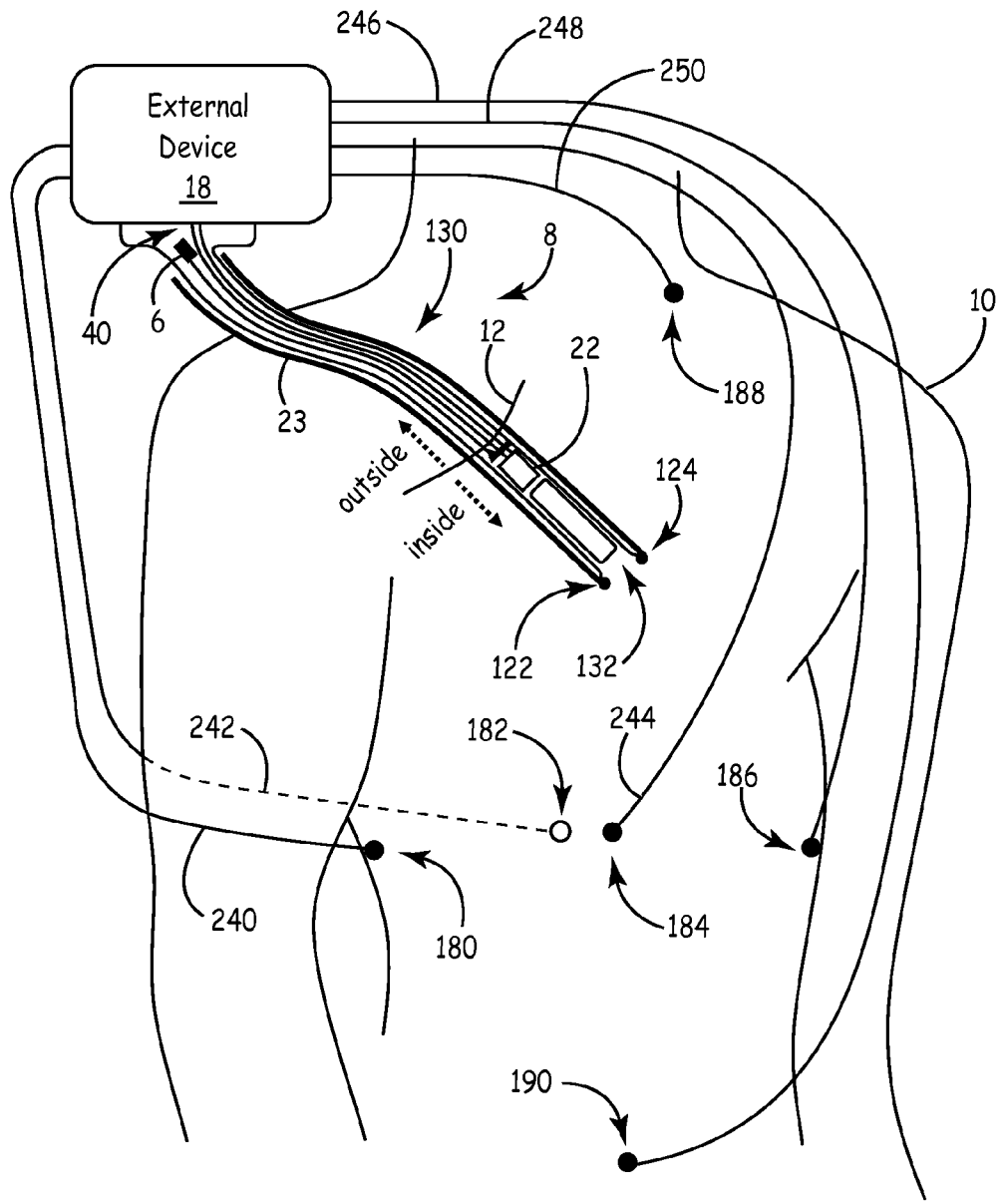
FIG. 18 is a schematic diagram illustrating an example delivery system with a plurality of electrodes placed on the body of the patient.

The plurality of electrodes 180, 182, 184, 186, 188, and 190 are used to test the communication signal quality with IMD 132 or telemetry coupling electrodes 122, 124. The external device 18 may measure the signal quality between telemetry coupling electrodes 122, 124 or telemetry electrodes of IMD 132 and each of the electrodes 180, 182, 184, 186, 188, and 190 and determine which is best. Further, the external device 18 may interpolate the measurements of the communication signal quality from the various electrodes to predict intermediate locations between the body electrodes 180, 182, 184, 186, 188, and 190 where the communication signal quality will likely provide the best communication between the IMD 132 and a body electrode. The plurality of electrodes illustrated in FIG. 18 is used for the localization described above using the LocaLisa™ and also for the assessment of communication signal quality. For localization systems such as the Axiem™ system, described above, the body electrodes do not serve for the localization and, therefore, need not be positioned for such purposes. When used with the Axiem™ system, the body electrodes may be placed in other locations (not shown) on the patient. In this example, the number and placement of body electrodes may be planned solely for the purpose of assessing communication signal quality. Understanding the IMD telemetry electrode orientation aids in predicting the area on the body where the best communication signal is expected as the maximum signal would occur along a vector which is normal to the unit vector between the two telemetry communication electrodes on the IMD 132. Upon predicting an intermediate location where the communication will be best, the external device 18 recommends a location for the placement of body electrodes 172, 174 (see FIG. 17) for subsequent follow-up procedures with the specific patient. Notation can be made in the patient's medical chart and the patient 10 informed as to the location required for the body electrode for successful communication with the IMD 132. The patient then reminds medical personnel, if the need arises, as to the location for telemetry with their IMD. If the IMD functions well in a particular location with respect to the therapeutic and monitoring clinical goals, the IMD is then implanted in the particular location and, if the particular location does not have other adverse consequences on the well being of the patient, requiring a special position for the communication with the IMD is a decision that may be made by the user.

The telemetry coupling electrodes 122, 124 on the distal end of the delivery system catheter may be used with the localization system to visualize the position and orientation of the telemetry coupling electrodes 122, 124. With this information, the user manipulates the delivery system catheter 130 while the external device 18 reports the communication signal quality. The external device 18 then develops a report and display of the communication signal quality as a function of the position of the distal portion of the delivery system catheter 130. In other words, the external device 18 may map the communication signal quality over the extent of the exploration. This report may aid in guiding the user to suitable locations for implantation of the IMD 132. The user then selects a site for permanent implantation. During manipulation of the delivery system catheter 23, the localization module 28 in the external device 18 provides guidance towards the selected site. For example, localization module 38 may display a three-dimensional view of the localization to provide visual cues as to distance and direction the distal end of the catheter 23 must be manipulated in order to move the delivery system catheter 23 and the IMD 132 to achieve the specific site and orientation of the IMD 132 for permanent implantation. In this manner, mapping the communication signal quality over the extent of the exploration by the user can be recorded and useful in the selection of a site for permanent implantation.

Figure 19:
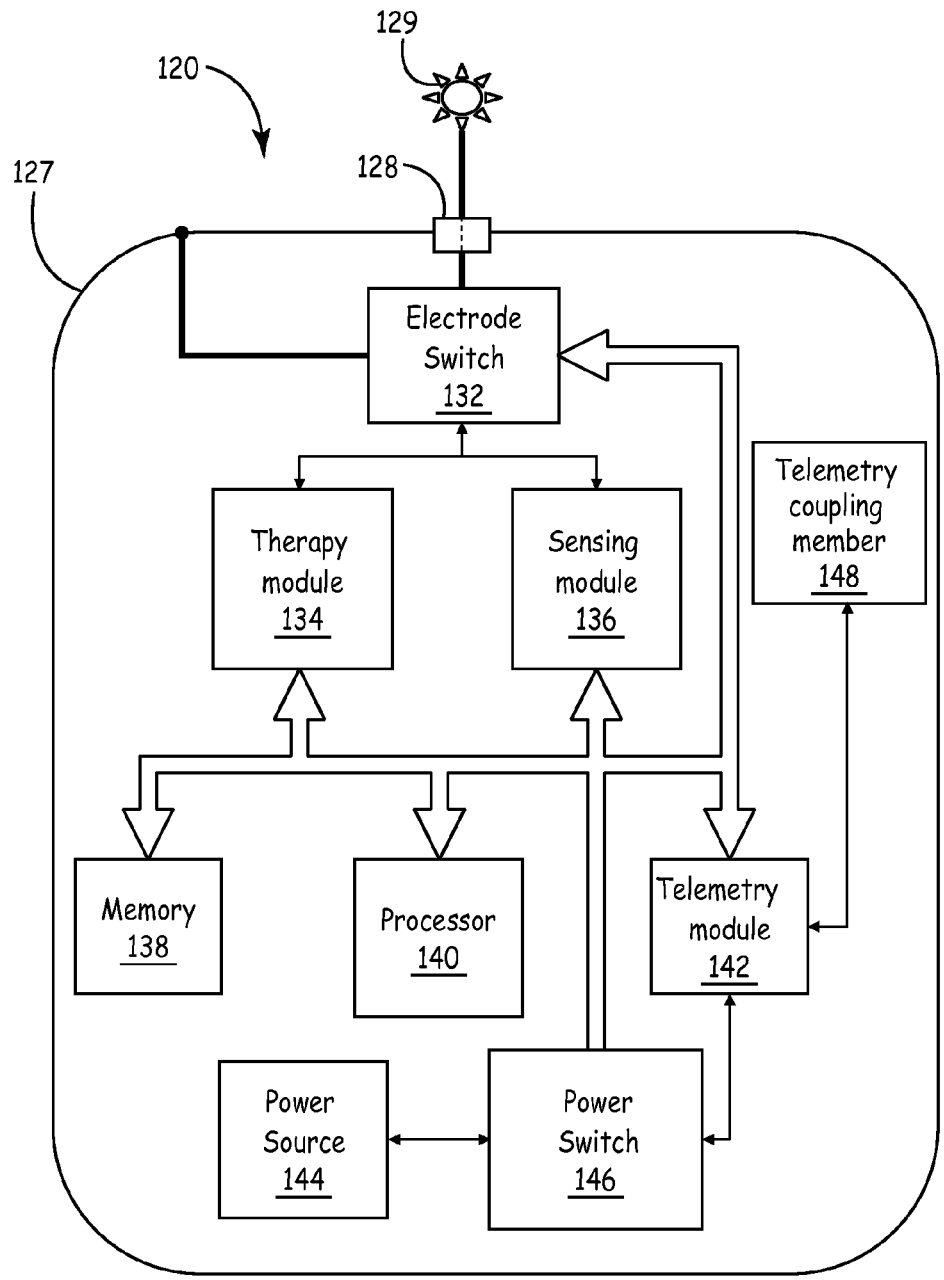
FIG. 19 is a schematic diagram illustrating an example IMD that may be delivered via a catheter.

FIG. 19 is a block diagram illustrating an example IMD 120 in further detail. IMD 120 includes a capsule 127 that houses the components of IMD 120 and an electrode 129 extending from capsule 127 via feed through 128. IMD 120 may correspond to any of IMDs 14, 36, 54, 76, 86, 94, or 104. Feed through 128 includes a conductor to connect to electrode 129 and insulate it from capsule 127 surrounding IMD 120. As described above, electrode 129 is placed within or adjacent to the target location, e.g., tissue, nerve, muscle or organ, of patient 10.

IMD 120 of FIG. 19 includes an electrode switch 133, a therapy module 134, a sensing module 136, a memory 138, a processor 140, a telemetry module 142, a telemetry coupling member 148, a power source 144 and a power switch 146 within capsule 127. The various components of IMD 120 are interconnected via one or more data buses or direct connections. IMD 120 may include more or fewer components than illustrated in FIG. 19 depending on the functionality provided by IMD 120. For example, IMD 120 may not include therapy module 134 in instances in which IMD 120 is designed for sensing or monitoring purposes only, such as an implantable loop recorder.

IMD 120 is configurable to operate in a number of different power states (shown in Table 1, below). IMD 120 uses a different amount of power in each of the power states. IMD 120 may operate in a first power state, referred to herein as a "ship state," during which no power is provided to any of the components of IMD 120. During the ship state, power switch 146 may be set to a first position to disconnect power source 144 from the other components of IMD 120. IMD 120 may be configured in the ship state during shipping from a manufacturing facility to a clinical facility. Power switch 146 operates with a very small current so as to not degrade the service life of the IMD 120. Components which may be utilized for the switching function within the power switch 146 are transistors, field effect transistors, MEMS switches or other component which offers low quiescent current drain.

Prior to being implanted, IMD 120 may be configured to operate in a second power state, referred to herein as an "implant state," during which power is provided to some or all of the other components of IMD 120. During the implant state, power switch 146 is set to a second position or state to couple power source 144 to at least some of the components of IMD 120. For example, IMD 120 may be configured from the ship power state to the implant power state in response to a telemetry signal of sufficient strength being received by IMD 120 so the power harvested by the IMD is sufficient to activate power switch 146.

During the implant state, telemetry module 142 operates in a low power state in which a transmitter of telemetry module 142 is set to a low transmit power and/or a receiver of telemetry module 142 is set to a low sensitivity. Telemetry module 142 may operate in this low power state during implantation due to the close proximity of telemetry coupling member 148 of IMD 120 and the telemetry coupling member of the delivery catheter, e.g., telemetry coupling member 22. In other words, the power required for reliable transmission between telemetry device 18 and IMD 120 is low due to the proximity of telemetry coupling member 148 of IMD 120 and telemetry coupling member 22 of the delivery catheter. As such, the power drain by telemetry module 142 is reduced as compared to the drain required for communication from IMD 120 to a device outside the body, such as external device 24. In this manner, power source 144 may be conserved with regards to the drain from the use of telemetry. In other instances, IMD 120 may not be configured into the implant state, but transition right to one of the power states described below.

After navigating IMD 120 to a target tissue location, IMD 120 may perform one or more tests to verify that IMD 120 functions as desired prior to releasing IMD 120 from the delivery catheter. For example, processor 140 may control therapy module 134 and sensing module 136 to measure a stimulation threshold, an impedance of the electrode-tissue interface as presented to IMD 120, an amplitude of sensed electrogram potentials from appropriate chambers of the heart, an amplitude of sensed electrogram potentials from other chambers of the heart, appropriate detection of various physiologic sensors within the IMD, hemodynamic consequences of pacing (e.g. cardiac output when paced from the selected location), any hemodynamic obstruction that may be caused by the IMD 120 as located in the heart.

Processor 140 may, in one instance, perform the one or more tests in response to signals or commands received by telemetry module 142 from an external device coupled to the delivery catheter in which IMD 120 is located, such as external device 18. In this case, processor 140 may control telemetry module 142 to transmit the results of the tests to the external device coupled to the delivery catheter to allow a user to assess the suitability of the implant location. In other instances, IMD 120 may not perform the test. Instead, an external device, such as external device 18 of FIG. 17 may perform these tests while the device operates in the ship state. In this case, IMD 120 may not operate in the implant state.

Additionally, IMD 120 may test the communicative coupling to IMD 120 or to other devices implanted or external to the patient. In this case, telemetry module 142 enters a high power state, referred to herein as a "Tele-Hi state." During the Tele-Hi state, the transmitter of telemetry module 142 operates at a higher power relative to the low power state and the receiver of telemetry module 142 operates at a higher sensitivity relative to the low power state to allow communication with external device 18 (e.g., external programmer) to be tested and verified before final release of IMD 120 within the body of patient 10. Telemetry module 142 operates in the Tele-Hi power state for this testing because of the increased distance from telemetry coupling member 148 of IMD 120 and an antenna of external device 18 is considerably further than the distance between telemetry coupling member 148 of IMD 120 and telemetry coupling member 22 of the delivery catheter. In other words, the longer telemetry distance requires a higher power for the transmitting and a higher sensitivity for the receiving in the IMD telemetry module 142. IMD 120 may also use the Tele-Hi power state when a telemetry session is initiated after implantation within patient 10, e.g., during a follow-up session.

After testing is performed, IMD 120 transitions to another power state that will be used during the majority of the service life of IMD 120. This state is referred to herein as the "service state." During the service state, telemetry module 142 may operate in a sleep mode or wakeup mode in which the transmitter of telemetry module 142 is turned OFF and the receiver of telemetry module 142 periodically scans for telemetry signals destined for IMD 120. By only periodically using the telemetry receiver function in telemetry module 142 and not using the telemetry transmit function, telemetry module 142 consumes only a small amount of power.

Table 1 provides a summary of the example power states of IMD 120. In Table 1, the column titled "circuit power" refers to the state of power switch 146, the column titled "Telemetry Transmit" refers to the mode of the transmitter of telemetry module 142 and the column titled "Telemetry Receive" refers to the mode of the receiver of telemetry module 142.

TABLE 1

| State | Circuit Power | Telemetry Transmit | Telemetry Receive |
|---|---|---|---|
| Ship | OFF | OFF | OFF |
| Implant | ON | Low Power | Low Sensitivity |
| Tele-Hi | ON | High Power | High Sensitivity |
| Service | ON | OFF | Periodic |

IMD 120 may, in some instances, further include electrode switch 133 that electrically couples therapy module 134 and sensing module 136 to electrode 129 when electrode switch 133 is closed and electrically isolates therapy module 134 and sensing module 136 from electrode 129 when electrode switch 133 is open. In one example, electrode switch 133 may be in the open position during the ship state and the implant state to isolate therapy module 134 and sensing module 136 from the electrode. Electrode switch 133 thus allows the electrical connections of electrode 129 to be disconnected during the process of navigating and positioning IMD 120 for implant. In this case, an external connection to electrode 129 may be utilized to test the suitability of electrode 129 for stimulating and sensing in the tissue of patient 10.

An external device, such as external device 18 or a device including an analyzer module, may verify the electrode-tissue properties, thus conserving power resources of IMD 120 that would have been used to perform the suitability testing/verification. Additionally, by removing the electrical connections to electrode 129 within IMD 120, precise electrical measurements of the stimulation threshold, the pacing impedance of the electrode and electrogram measurements of the slew rate and the amplitude of the tissue depolarizations may be made without the adverse effects of a parallel impedance derived from the circuitry within IMD 120. These measurements allow an assessment of electrode 129 to ensure the adequate long-term performance and to ensure the electrode is lodged in viable tissue. After performing the suitability testing using the external connection, electrode switch 133 may be closed to electrically connect therapy module 134 and sensing module 136 to electrode 129.

In other embodiments, however, IMD 120 performs the measurements to test the suitability of IMD 120 to perform its desired functions at the proposed location of implant. In this example, IMD 120 may not include an electrode switch 133. Instead, the electrode may be directly connected to pacing module 134 and sensing module 136 via feed through 126 at all times. The measurements performed by IMD 120 may be transmitted to external device 18 or other external device via telemetry coupling member 148 of the delivery catheter.

Data and control information is exchanged within IMD 120 as shown in FIG. 19 between electrode switch 133, therapy module 134, sensing module 136, memory 138, processor 140, telemetry module 142 and power switch 146. Memory 138 contains the data used for operating processor 140 and analyzing the performance of IMD 120. Memory 138 may include computer-readable instructions that, when executed by processor 140 or other component of IMD 120, cause one or more components of IMD 120 to perform various functions attributed to those components in this disclosure, including any suitability testing, therapy functions, sensing functions, status monitoring functions, telemetry functions, or the like. The instructions may be pre-programmed instructions or instructions received from telemetry module 142 from an external device.

Memory 138 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media. Processor 140 may include any one or more of a microprocessor, a controller, a digital signal processors (DSPs), application specific integrated circuits (ASICs), field-programmable gate arrays (FPGAs), or equivalent discrete or integrated circuitry, including analog circuitry, digital circuitry, or logic circuitry. The functions attributed to processor 140 herein may be embodied as software, firmware, hardware or any combination thereof.

Telemetry module 142 may receive downlink telemetry from and send uplink telemetry to another device with the aid of telemetry coupling member 148, which may be internal and/or external to IMD 120. During the delivery and the implantation of IMD 120, telemetry information may be exchanged with an external device (e.g., external device 18) using IMD telemetry coupling member 148 and telemetry module 142. As described above, IMD telemetry coupling member 148 may be communicatively coupled with the external device via a telemetry coupling member 22 and feed line 16 within the delivery catheter. Although FIG. 19 is described in the context of antennas, IMD 120 may be communicatively coupled to the external device via a different telemetry coupling member, such as a transducer, an electrical connection, a capacitor(s), or the like.

After implantation of IMD 120 within patient 10, IMD 120 may communicate with an external device 18, or an embodiment such as a programming device. IMD 120 may communicate with external device 18 coupled to the delivery catheter used to implant IMD 120. For example, IMD 120 and external device 18 may communicate using the same communication techniques used to communicate between IMD 120 and telemetry device 18, but with different amounts of power consumption. As described above, IMD 120 may operate telemetry module 142 in a low power mode (e.g., low transmit power and low receiver sensitivity) to communicate with the external device 18 when not using the telemetry coupling member as when coupled to the delivery catheter and operate telemetry module 142 in a higher power mode (e.g., with a high transmit power and high receiver sensitivity relative to the low power mode) to communicate with external device 24. In other instances, the communication techniques between IMD 120 and external device 24 may be different than the communication techniques used to communicate between IMD 120 and the external device coupled to delivery catheter 20, as described further below.

Telemetry module 142 includes any suitable hardware, firmware, software or any combination thereof for communicating with another device, such as programming device 18. For example, telemetry module 142 may include appropriate modulation, demodulation, encoding, decoding, frequency conversion, filtering, and amplifier components for transmission and reception of data. In instances in which IMD 120 communicates with external device 18 using a different communication technique than used when in the delivery catheter, telemetry module 142 may include more than one set of telemetry components (e.g., modulation, demodulation, encoding, decoding, frequency conversion, filtering, and amplifier, antenna components or the like), e.g., one set for each type of communication.

Power source 144 contains an energy source for powering the components within IMD 120. Power source 144 may include a rechargeable or non-rechargeable battery. A non-rechargeable battery may be capable of holding a charge for several years, while a rechargeable battery may be inductively charged from an external device, e.g., on a daily or weekly basis. In some instances, power source 144 may harvest energy during the implantation, e.g., by harvesting the power from the telemetry system in the telemetry module 142.

IMD 120 may include one or more sensors in addition to electrode 129. The sensors may be located within IMD 120, attached to an external surface of IMD 120 or may be remote to IMD 120 and may communicate with IMD 120 wirelessly. In the example of an implantable cardiac pacemaker, IMD 120 may comprise more electrodes which are on the outside of or external to IMD 120. Other sensors within IMD 120 may also be utilized, including an accelerometer, a temperature sensor, optical tissue sensor or a GPS receiver. Sensors outside IMD 120 may include electrodes associated with measuring impedance of various tissues within the body, a pressure sensor, a temperature sensor, a chemical sensor or other sensors.

Figure 20:
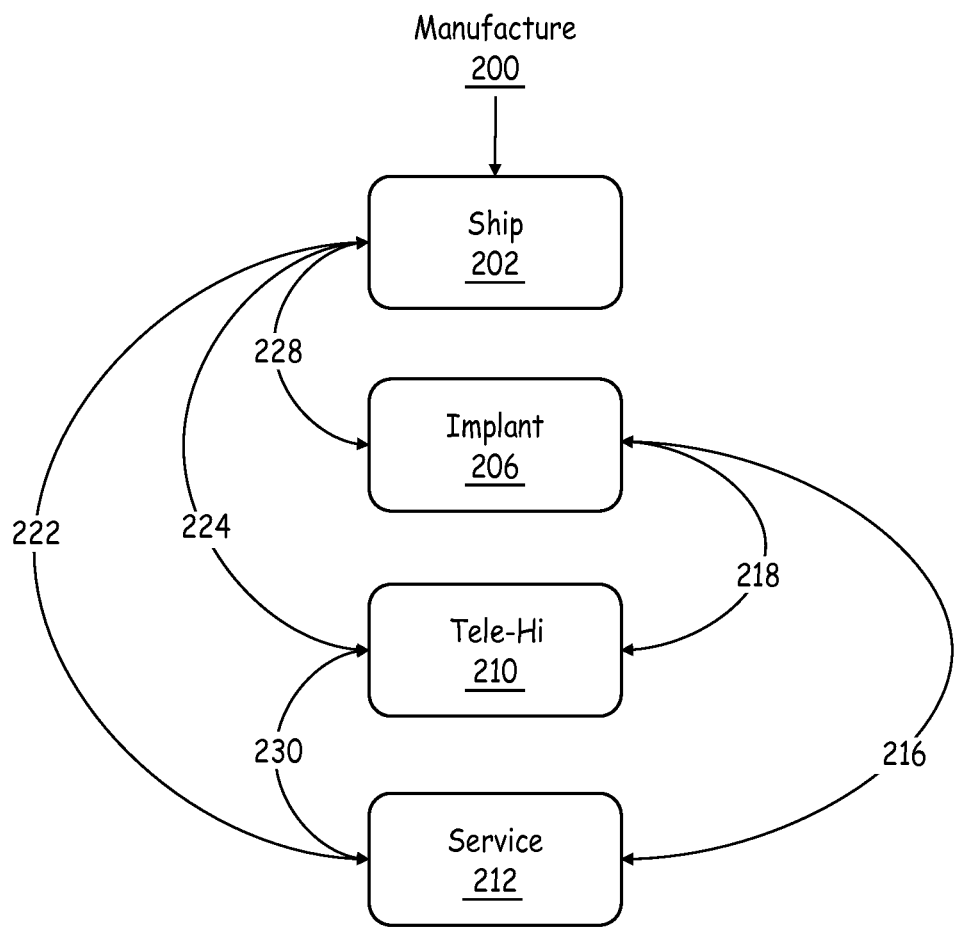
FIG. 20 is a state diagram of four states and transitions between those states.

FIG. 20 is a state diagram illustrating an example set of power states of an IMD along with transitions between the various power states. FIG. 20 will be described with respect to IMD 120 for purposes of discussion. However, IMDs 14, 36, 54, 76, 86, 94 and 104 may operate and transition between similar power states. Upon manufacture 200, IMD 120 is placed in ship state 202. As described above, ship state 202 refers to a state in which no power is provided to any of the components of IMD 120. For example, power switch 146 of IMD 120 may be opened to disconnect power source 144 from the other components of IMD 120. IMD 120 may be configured in the ship state during shipping from a manufacturing facility to a clinical facility.

IMD 120 may transition from ship state 202 to any of the other states (e.g., transitions 222, 224, or 228) in response to receiving a telemetry signal of sufficient strength. For example, IMD 120 may harvest power from the telemetry signal and close power switch 146 upon harvesting enough power from the telemetry signal. In other words, IMD 120 may power the components of IMD 120 in response to a telemetry signal of a sufficient strength. In addition, IMD 120 may receive a signal designating the next state into which to configure IMD 120. The signal may designate any of the available states, e.g., implant state 206, Tele-Hi state 210 or service state 212. Alternatively, IMD 120 may be configured into a default state upon powering up, such as implant state 206.

For purposes of discussion, assume that IMD 120 enters implant state 206 in which power is provided to some or all of the other components of IMD 120. During the implant state, telemetry module 142 operates in a low power mode in which a transmitter of telemetry module 142 is set to a low transmit power and/or a receiver of telemetry module 142 is set to a low sensitivity. From the implant state 206, low power telemetry from an adjacent antenna (or other telemetry coupling means) or high power telemetry from a distant antenna and the appropriate message directs the IMD 120 to transitions 216 or 218.

Tele-Hi state 210 refers to state in which the telemetry module 142 operates in a high power mode where the transmitter operates at a higher power and the receiver operates at a higher sensitivity relative to the low power state. IMD 120 may, for example, operate in Tele-Hi state 210 to allow communication with external device 24 to be tested and verified before final release of IMD 120 within the body of patient 10. IMD 120 may also use the Tele-Hi state 210 when a telemetry session is initiated after implantation within patient 10, e.g., during a follow-up session. When the IMD is in Tele-Hi state 210, high power telemetry or a time out within IMD 120 causes transition 230 to reach service state 212.

Service state 212 refers to a state in which therapy module 134 and sensing module 136 operate to perform their functions, and telemetry module 142 operates in a sleep mode or wakeup mode in which the transmitter of telemetry module 142 is turned OFF and the receiver of telemetry module 142 periodically scans for telemetry signals destined for IMD 120. By only periodically using the telemetry receiver function in telemetry module 142 and not using the telemetry transmit function, telemetry module 142 consumes only a small amount of power. A high power telemetry message may cause IMD 120 to leave service state 212 with transitions 222, 216 or 230.

Figure 21:
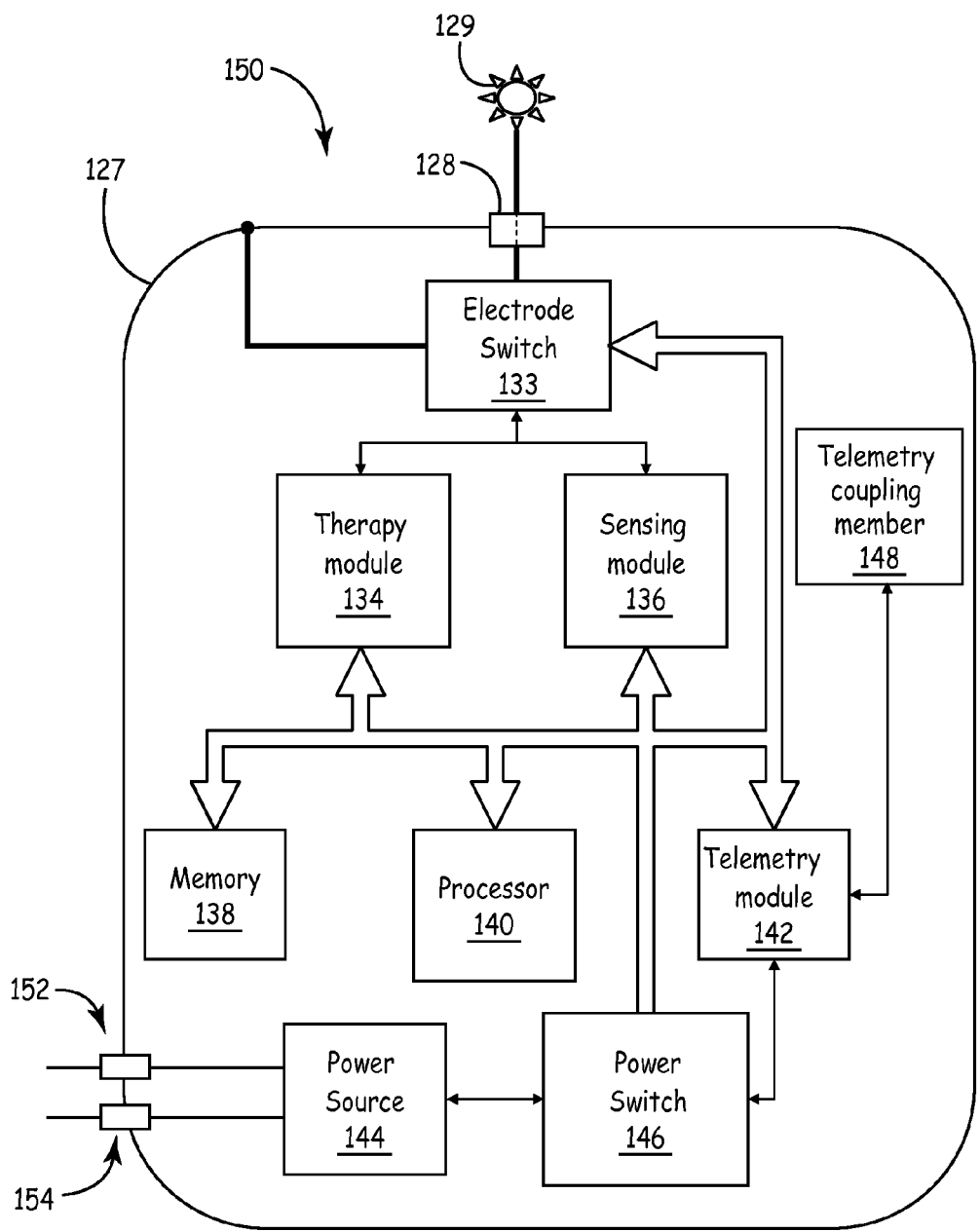
FIG. 21 is a schematic diagram illustrating an example IMD with direct electrical power connections.

FIG. 21 illustrates a block diagram of another example IMD 150 in further detail. IMD 150 of FIG. 21 is substantially similar to IMD 120 of FIG. 19, but includes connectors 152, 154 to receive power from an external source during delivery, navigation and implantation of IMD 150. Detachable connectors 152 and 154 are provided to connect to power conductors within the delivery system catheter.

Figure 22:
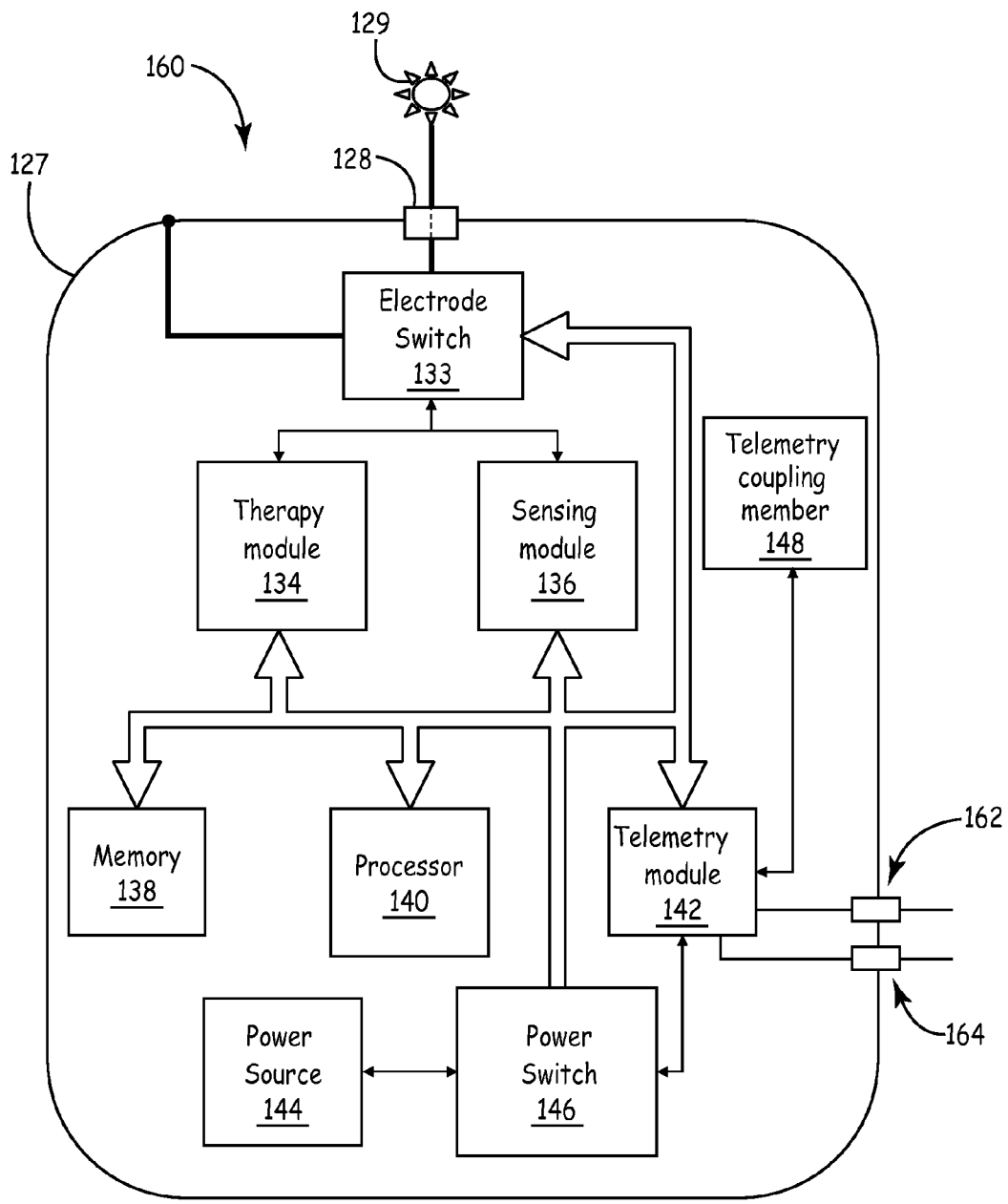
FIG. 22 is a schematic diagram illustrating an example IMD with direct electrical telemetry connections.

FIG. 22 illustrates a block diagram of another example IMD 160 in further detail. IMD 160 of FIG. 22 is substantially similar to IMD 120 of FIG. 19, but includes connectors 162, 164 provide external connections for telemetry, in a similar manner as described in FIG. 10. As the telemetry circuit can harvest power from the telemetry signals, this embodiment allows the transfer of telemetry and/or power through the feed throughs and connectors 162, 164.

Figure 23:
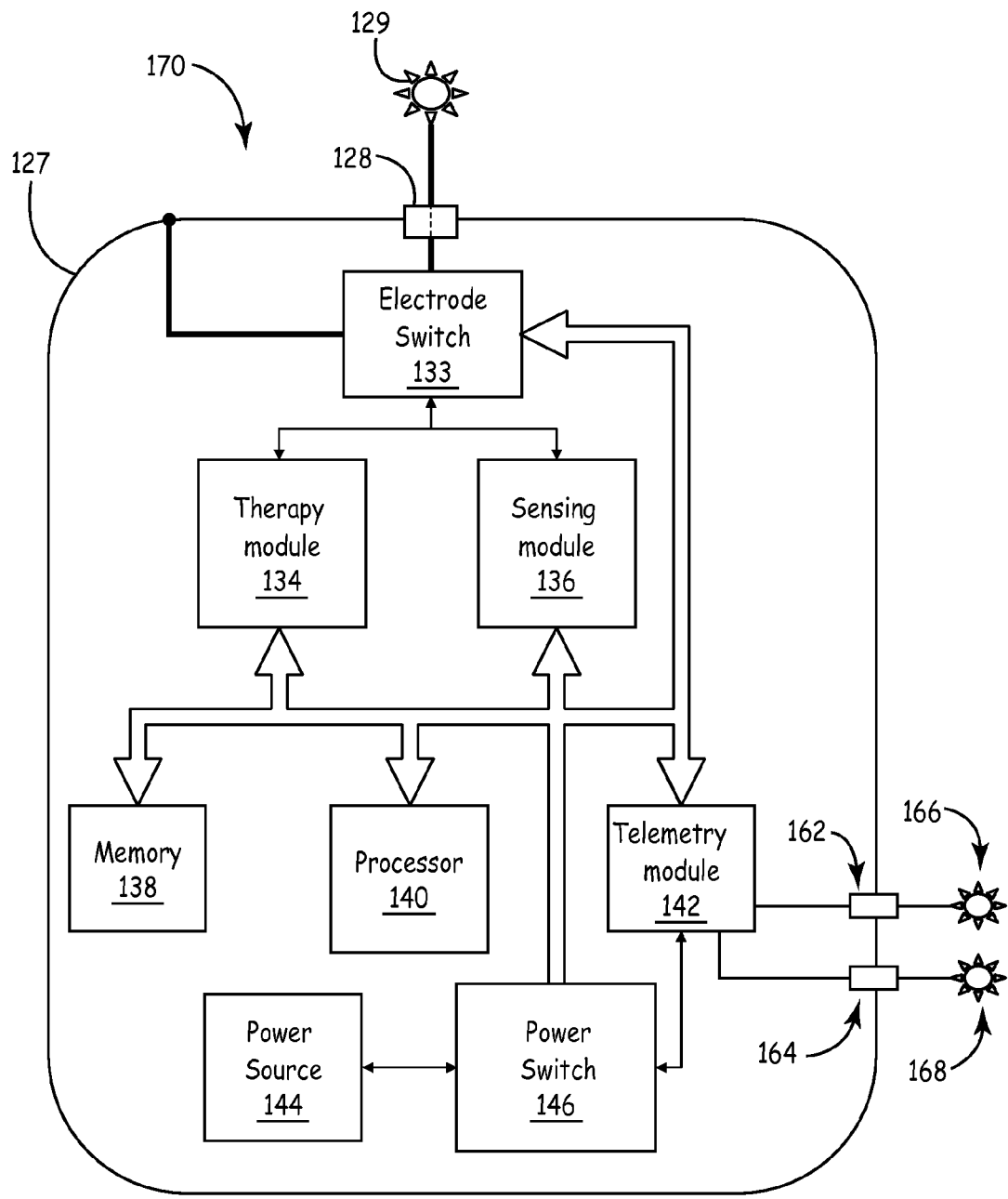
FIG. 23 is a schematic diagram illustrating an example IMD with telemetry electrodes.

FIG. 23 illustrates a block diagram of another example of IMD 170 in further detail. IMD 170 of FIG. 23 is substantially similar to IMD 120 of FIG. 22, but includes telemetry electrodes 166, 168 for conductively coupled communication through the body. In some instances, one or both of telemetry electrodes 166, 168 may be used for conductively coupled communication through the body as well as delivery of therapy. In such instances, IMD 170 may not include a separate therapy electrode 129.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. Although the channel recovery techniques of this disclosure are described in the context of a two-staged channel recovery (i.e., same channel recovery followed by unspecified channel recovery), the techniques may be used in a single stage channel recovery. For example, channel recovery may be performed using the telemetry wakeup feature immediately after or soon after loss of the communication session is detected. In other words, there may be no same channel recovery performed in the native mode. These and other examples are within the scope of the following claims.

The invention claimed is:

1. An implantable medical device delivery system comprising:
   a catheter configured to be located at least partially within a patient, the catheter comprising:
      an elongate catheter body having a proximal end and a distal end, the distal end configured to be located within the patient;
      at least two telemetry coupling electrodes located on the distal end of the catheter body; and
      a feed line coupled to the at least two telemetry coupling electrodes;
   at least one body electrode configured for placement on the patient; and
   an external device, located outside of the patient, coupled to the feed line at the proximal end of the catheter and to the body electrode,
   wherein the external device is configured to:
      generate and receive a telemetry communication signal that is communicated through the patient between the body electrode and the telemetry coupling electrodes;
      measure at least one parameter of the telemetry communication signal indicative of a quality of the telemetry communication signal for communication of data;
      determine the quality of the telemetry communication signal for communication of data based on the measurement of the at least one parameter; and
      report the quality of the telemetry communication signal to a user of the external device.

2. The system of claim 1, wherein the external device is further configured to predict a future telemetry communication signal quality between an implanted medical device and the external device based on the quality of the telemetry communication signal between the body electrode and the telemetry coupling electrodes.

3. The system of claim 1, wherein the at least one body electrode is one of a plurality of body electrodes configured for placement on the patient, each of which is coupled to the external device, the system further comprising:
   a localization module that generates position information defining positions of the telemetry coupling electrodes within the patient using a plurality of signals communicated between the plurality of body electrodes and the at least two telemetry coupling electrodes, wherein the external device is configured to measure the at least one parameter of the telemetry communication signal indicative of the quality of the telemetry communication signal between the plurality of body electrodes and the telemetry coupling electrodes for communication of data at various positions of the telemetry coupling electrodes and to store the position information generated by the localization module and the measurement of the at least one parameter indicative of the quality of the telemetry communication signal at the various positions.

4. The system of claim 3, wherein the localization module generates position information using signals communicated between at least one of:

the plurality of body electrodes and the at least two telemetry coupling electrodes;

the plurality of body electrodes and an implantable electrode coupled to an implantable medical device; or a sensor at the distal end of the catheter and the localization module.

5. The system of claim 3, wherein the external device is further configured to predict the quality of the telemetry communication signal through the patient between the external device and an implantable medical device, once implanted, such that telemetry electrodes on the implantable medical device are in substantially the same positions as the telemetry coupling electrodes at the time of the position measurements, as a function of the position information.

6. The system of claim 5, wherein the external device is further configured to recommend a suitable position and associated orientation for permanent implant of the implantable medical device.

7. The system of claim 3, wherein the external device is further configured to recommend one or more body electrode positions for successful communication with an implantable medical device, were the device implanted, such that a plurality of telemetry electrodes on the implantable medical device are in substantially the same positions as the telemetry coupling electrodes.

8. The system of claim 1, wherein the at least one parameter indicative of the quality of the telemetry communication signal for communication of data comprises at least one of a transmission power for detection of the signal, a received signal strength, a received signal to noise ratio, a bit error rate, a data throughput rate, a data dropout rate, or a background noise floor.

* * * * *